United States Patent [19]
Wickham et al.

[11] Patent Number: 5,965,541
[45] Date of Patent: *Oct. 12, 1999

[54] VECTORS AND METHODS FOR GENE TRANSFER TO CELLS

[75] Inventors: Thomas J. Wickham, Potomac; Imre Kovesdi, Rockville; Douglas E. Brough, Olney, all of Md.

[73] Assignee: GenVec, Inc., Rockville, Md.

[ * ] Notice: This patent is subject to a terminal disclaimer.

[21] Appl. No.: 08/563,368

[22] Filed: Nov. 28, 1995

[51] Int. Cl.⁶ .................................................. A01N 43/04
[52] U.S. Cl. ...................... 514/44; 435/69.1; 435/320.1; 435/367; 435/379; 435/370; 435/456; 530/350; 536/23.4; 536/23.72
[58] Field of Search .............................. 435/320.1, 69.7, 435/172.1, 172.3, 69.1, 367, 369, 370, 456; 536/24.2, 23.4, 23.72; 935/22, 23, 32, 57; 514/44; 530/350

[56] References Cited

U.S. PATENT DOCUMENTS

| | | | |
|---|---|---|---|
| 4,593,002 | 6/1986 | Dulbecco | 435/172.3 |
| 5,223,409 | 6/1993 | Ladner et al. | . |
| 5,403,484 | 4/1995 | Ladner et al. | . |
| 5,543,328 | 8/1996 | McClelland et al. | 435/320.1 |
| 5,547,932 | 8/1996 | Curiel et al. | . |
| 5,559,099 | 9/1996 | Wickham et al. | . |
| 5,571,698 | 11/1996 | Ladner et al. | . |
| 5,661,133 | 8/1997 | Leiden et al. | 514/44 |
| 5,672,344 | 9/1997 | Kelley et al. | 424/93.2 |
| 5,674,722 | 10/1997 | Mulligan et al. | 435/440 |

FOREIGN PATENT DOCUMENTS

| | | | |
|---|---|---|---|
| WO 92/02553 | 2/1992 | WIPO | C07K 15/00 |
| WO 94/10323 | 5/1994 | WIPO | C12N 15/87 |
| WO 94/17832 | 8/1994 | WIPO | A61K 48/00 |
| WO 95/05201 | 2/1995 | WIPO . | |
| WO 95/21259 | 8/1995 | WIPO | C12N 15/63 |
| WO 95/26412 | 10/1995 | WIPO . | |
| WO 95/31566 | 11/1995 | WIPO | C12N 15/86 |

OTHER PUBLICATIONS

Falck–Pedersen, Abstract of National Institutes of Health Grant Application No. 1 P01 HL51746–01UB: 0004 entitled "Gene Therapy For Cystic Fibrosis" (1994).
Barinaga, M. Science, vol. 226, p. 1326, 1994.
Marshall, E. Science, vol. 269, pp. 1050–1055, 1995.
Crystal, R. Science, vol. 270, pp. 404–410, 1995.
Jolly, D. Cancer Gene Therapy, vol. 1(1), pp. 51–64, 1994.
Orkin et al. Report and Recommendations of the Panel to Assess the NIH Investment in Research on Gene Therapy, 1995.
Hong et al., *Virology*, 185, 758–767 (1991).
Karyan et al., *Virology*, 202, 782–785 (1994).
Database WPI, Week 9316, Derwent Publications Ltd., AN 93–134470/16 (WO 93/07283 English abstract).
Database WPI, Week 9440, Derwent Publications Ltd., AN 94–317775/40 (WO 94/24299 English abstract).
Batra et al., *Gene Therapy*, 1, 255–260 (1994).
Boursnell et al., *Gene*, 13, 311–317 (1981).
Chu et al., *Gene Therapy*, 292–299 (1994).
Cotten et al., *Proc. Natl. Acad. Sci.*, 87, 4033–4037 (1990).
Crystal, *Science*, 270, 404–410 (1995).
Han et al., *Proc. Natl. Acad. Sci.*, 92, 9747–9751.
Horvath et al., *J. Virol.*, 62, 341–345 (1988).
Huang et al., *J. Virol.*, 69, 2257–2263 (1995).
Maraveyas et al., *Acta Oncologica*, 32, 741–746 (1993).
Mastrangeli et al., *Ped. Pulm.*, Suppl. 12, 230, Ab. No. 180 (1995).
Mastrangeli et al., *Human Gene Therapy*, 7, 79–87 (1996).
Michael et al., *The Journal of Biological Chemistry*, 268, 6866–6869 (1993).
Michael et al., *Gene Therapy*, 660–668 (1995).
Miller et al., *FASEB J.*, 9, 190–199 (1995).
Neda et al., *J. Biol. Chem.*, 266, 14143–14146 (1991).
Russell et al., *Nucleic Acids Research*, 21, 1081–1085 (1993).
Silver et al., *Virology*, 165, 377–387 (1988).
Wickham et al., *J. Cell. Biol.*, 127, 257–264 (1994).
Wickham et al., *Gene Therapy*, 2, 750–756 (1995).
Chroboczek et al., *Virology*, 186, 280–285 (1992).
Cotten et al., *Proc. Natl. Acad. Sci.*, 89, 6094–6098 (1992).
Curiel et al., *Proc. Natl. Acad. Sci.*, 88, 8850–8854 (1991).
Curiel et al., *Human Gene Therapy*, 3, 147–154 (1992).
Defer et al., *Journal of Virology*, 64(8), 3661–3673 (1990).
Dupuit et al., *Human Gene Therapy*, 6, 1185–1193 (1995).
Falgout et al., *Journal of Virology*, 62, 622–625 (1988).
Grubb et al., *Nature*, 371, 802–806 (1994).
Kass–Eisler et al., *Proc. Natl. Acad. Sci.*, 90, 11498–11502 (1993).
Mathias et al., *Journal of Virology*, 68, 6811–6814 (1994).
Michael et al., *Adenovirus Workshop*, St. Andrews University, 52, 13–15 (1995).
Nemerow et al., *In Biology of Vitronectins and Their Receptors*, Preissner et al., eds., 177–184 (Elsevier Science Publishers).
Nemerow et al., *Trends in Cell Biology*, 4, 52–55 (1994).
Novelli et al., *Virology*, 185, 365–376 (1991).
Signas et al., *Journal of Virology*, 53(2), 672–678 (1985).
Wagner et al., *Proc. Natl. Acad. Sci.*, 89, 6099–6103 (1992).
Watson et al., *Journal of Virology*, 69, 525–535 (1988).
Wickham et al., *Cell*, 73, 309–319 (1993).

*Primary Examiner*—James Ketter
*Assistant Examiner*—Irem Yucel
*Attorney, Agent, or Firm*—Leydig, Voit & Mayer, Ltd.

[57] ABSTRACT

The present invention provides a chimeric adenovirus coat protein, which differs from the wild-type coat protein by the introduction of a nonnative amino acid sequence. Such a chimeric adenovirus coat protein according to the invention is able to direct entry into cells of a vector comprising the coat protein that is more efficient than entry into cells of a vector that is identical except for comprising a wild-type adenovirus coat protein rather than the chimeric adenovirus coat protein. The chimeric coat protein preferably is a fiber, hexon, or penton protein. The present invention also provides an adenoviral vector that comprises the chimeric adenovirus coat protein, as well as methods of constructing and using such a vector.

62 Claims, 11 Drawing Sheets

```
Ala Gln Glu *
GCC CAA GAA TAA AGA ATC GTT TGT GTT ATG TTT CAA CGT        [SEQ ID NO:13]

TRANSCRIPTION

GCC CAA GAA UAA AGA AUC GUU UGU GUU AAA AAA AAA AAA AAA ..... [SEQ ID NO:14]

TRANSLATION

Ala Gln Glu *
```

FIG. 2A

Ala Gln Glu Gly Ser Asn Lys Glu Ser Phe Val Leu Cys [SEQ ID NO:16]

GCC CAA GAA GGA TCC AAT AAA GAA TCG TTT GTG TTA TGT [SEQ ID NO:15]
            BamHI  PolyA

TRANSCRIPTION

GCC CAA GAA GGA UCC AAU AAA GAA UCG UUU GUG UUA AAA AAA AAA AAA AAA AAA... [SEQ ID NO:17]

TRANSLATION

Ala Gln Glu Gly Ser Asn Lys Glu Ser Phe Val Leu Lys Lys Lys Lys Lys Lys... [SEQ ID NO:18]

FIG. 2B

TAT GGA GGA TCC AAT AAA GAA TCG TTT GTG TTA TGT TTC AAC GTG TTT ATT TTT C [SEQ ID NO:9]

Ndel BamHI  PolyA                                                   polyA   MunI

FIG. 4A

AAT TGA AAA ATA AAC ACG TTG AAA CAT AAC ACA AAC GAT TCT TTA TTG GAT CCT CCA [SEQ ID NO:10]

MunI  PolyA                                                         BamHI  Ndel

FIG. 4B

TCCC CCCGGG TCTAGA TTA GGA TCC TCC TTG GGC AAT GTA TGA [SEQ ID NO:11]

XmaI  XbaI  Stop BamHI

FIG. 4C

CGT GTA TCC ATA TGA CAC AGA [SEQ ID NO:12]

Ndel

FIG. 4D

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Lys Lys Lys Lys Lys Lys Lys Lys
   1          5

(2) INFORMATION FOR SEQ ID NO:2:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Arg Arg Arg Arg Arg Arg Arg Arg
   1          5

(2) INFORMATION FOR SEQ ID NO:3:

(i) SEQUENCE CHARACTERISTICS:
      (A) LENGTH: 8 amino acids
      (B) TYPE: amino acid

```
            (C) STRANDEDNESS: single
            (D) TOPOLOGY: linear (ii) MOLECULE TYPE: peptide (ix) FEATURE:
            (C) OTHER INFORMATION: Xaa is Lys or Arg (xi) SEQUENCE DESCRIPTION: SEQ ID NO:3:

Xaa Xaa Xaa Xaa Xaa Xaa Xaa Xaa
     1               5

(2) INFORMATION FOR SEQ ID NO:4:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Gly Ser Asn Lys Glu Ser Phe Val Leu Lys Lys Lys
     1               5                   10

(2) INFORMATION FOR SEQ ID NO:5:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Ala Gly Ser Asn Lys Asn Lys Glu Ser Phe Val Leu Lys Lys Lys
     1               5                   10                  15

(2) INFORMATION FOR SEQ ID NO:6:

(i) SEQUENCE CHARACTERISTICS:
            (A) LENGTH: 8 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:6:

GGA TCC AA                                                          8
Gly Ser
1

(2) INFORMATION FOR SEQ ID NO:7:

(i) SEQUENCE CHARACTERISTICS:
            (A) LENGTH: 30 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:7:

GGA TCC AAT AAA GAA TCG TTT GTG TTA TGT                            30
Gly Ser Asn Lys Glu Ser Phe Val Leu Cys
1               5                   10
```

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

```
GCC GGA TCC AAC AAG AAT AAA GAA TCG TTT GTG TTA           36
Ala Gly Ser Asn Lys Asn Lys Glu Ser Phe Val Leu
1               5                   10
```

(2) INFORMATION FOR SEQ ID NO:9:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:9:

```
TATGGAGGAT CCAATAAAGA ATCGTTTGTG TTATGTTTCA ACGTGTTTAT TTTTC    55
```

(2) INFORMATION FOR SEQ ID NO:10:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:10:

```
AATTGAAAAA TAAACACGTT GAAACATAAC ACAAACGATT CTTTATTGGA TCCTCCA   57
```

(2) INFORMATION FOR SEQ ID NO:11:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:11:

```
TCCCCCCGGG TCTAGATTAG GATCCTTCTT GGGCAATGTA TGA                 43
```

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:12:

```
CGTGTATCCA TATGACACAG A                                         21
```

(2) INFORMATION FOR SEQ ID NO:13:

(i) SEQUENCE CHARACTERISTICS:

31

(A) LENGTH: 39 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:13:

```
GCC CAA GAA TAA AGA ATC GTT TGT GTT ATG TTT CAA CGT          39
Ala Gln Glu
1
```

(2) INFORMATION FOR SEQ ID NO:14:

(i) SEQUENCE CHARACTERISTICS:
           (A) LENGTH: 48 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:14:

```
GCC CAA GAA UAA AGA AUC GUU UGU GUU AAA AAA AAA AAA AAA AAA  48
Ala Gln Glu
1
```

(2) INFORMATION FOR SEQ ID NO:15:

(i) SEQUENCE CHARACTERISTICS:
           (A) LENGTH: 39 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:15:

```
GCC CAA GAA GGA TCC AAT AAA GAA TCG TTT GTG TTA TGT          39
Ala Gln Glu Gly Ser Asn Lys Glu Ser Phe Val Leu Cys
1               5                   10
```

(2) INFORMATION FOR SEQ ID NO:16:

(i) SEQUENCE CHARACTERISTICS:
           (A) LENGTH: 13 amino acids
           (B) TYPE: amino acid
           (D) TOPOLOGY: linear (ii) MOLECULE TYPE: peptide (xi) SEQUENCE DESCRIPTION: SEQ ID NO:16:

```
Ala Gln Glu Gly Ser Asn Lys Glu Ser Phe Val Leu Cys
1               5                   10
```

(2) INFORMATION FOR SEQ ID NO:17:

(i) SEQUENCE CHARACTERISTICS:
           (A) LENGTH: 51 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:17:

```
GCC CAA GAA GGA UCC AAU AAA GAA UCG UUU GUG UUA AAA AAA AAA AAA AAA  51
Ala Gln Glu Gly Ser Asn Lys Glu Ser Phe Val Leu Lys Lys Lys Lys Lys
1               5                   10                  15
```

-continued (2) INFORMATION FOR SEQ ID NO:18:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:18:

```
Ala Gln Glu Gly Ser Asn Lys Glu Ser Phe Val Leu Lys Lys Lys Lys Lys
1               5                   10                  15
```

(2) INFORMATION FOR SEQ ID NO:19:

(i) SEQUENCE CHARACTERISTICS:
        (A) LENGTH: 62 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:19:

```
CATATGGAGG ATCCAATAAA GAATCGTTTG TGTTATGTTT CAACGTGTTT ATTTTTCAAT    60

TG                                                                  62
```

VECTORS AND METHODS FOR GENE TRANSFER TO CELLS

TECHNICAL FIELD OF THE INVENTION

The present invention pertains to a chimeric adenovirus coat protein which is able to direct entry into cells of a vector comprising the coat protein that is more efficient than a similar vector having a wild-type adenovirus coat protein. Such a chimeric coat protein is a fiber, hexon, or penton protein. The present invention also pertains to a recombinant vector comprising such a chimeric adenoviral coat protein, and to methods of constructing and using such a vector.

BACKGROUND OF THE INVENTION

Adenoviruses belong to the family Adenoviridae, which is divided into two genera, namely Mastadenovirus and Aviadenovirus. Adenoviruses are nonenveloped, regular icosahedrons of about 65 to 80 nanometers in diameter (Horne et al., *J. Mol. Biol.*, 1, 84–86 (1959)). The adenoviral capsid is composed of 252 capsomeres of which 240 are hexons and 12 are pentons (Ginsberg et al., *Virology*, 28, 782–783 (1966)). The hexons and pentons are derived from three different viral polypeptides (Maizel et al., *Virology*, 36, 115–125 (1968); Weber et al., *Virology*, 76, 709–724 (1977)). The hexon comprises three identical polypeptides of 967 amino acids each, namely polypeptide II (Roberts et al., *Science*, 232, 1148–1151 (1986)). The penton contains a penton base, which is bound to the capsid, and a fiber, which is noncovalently bound to and projects from the penton base. The fiber protein comprises three identical polypeptides of 582 amino acids each, namely polypeptide IV. The adenovirus serotype 2 (Ad2) penton base protein is a ring-shaped complex composed of five identical protein subunits of 571 amino acids each, namely polypeptide III (Boudin et al., *Virology*, 92, 125–138 (1979)). Proteins IX, VI, and IIIa are also present in the adenoviral coat and are thought to stabilize the viral capsid (Stewart et al., *Cell*, 67, 145–154 (1991); Stewart et al., *EMBO J.*, 12(7), 2589–2599 (1993)).

Once an adenovirus attaches to a cell, it undergoes receptor-mediated internalization into clathrin-coated endocytic vesicles of the cell (Svensson et al., *J. Virol.*, 51, 687–694 (1984); Chardonnet et al., *Virology*, 40, 462–477 (1970)). Virions entering the cell undergo a stepwise disassembly in which many of the viral structural proteins are shed (Greber et al., *Cell*, 75, 477–486 (1993)). During the uncoating process, the viral particles cause disruption of the cell endosome by a pH-dependent mechanism (Fitzgerald et al., *Cell*, 32, 607–617 (1983)), which is still poorly understood. The viral particles are then transported to the nuclear pore complex of the cell (Dales et al., *Virology*, 56, 465–483 (1973)), where the viral genome enters the nucleus, thus initiating infection.

An adenovirus uses two separate cellular receptors, both of which must be present, to efficiently attach to and infect a cell (Wickham et al., *Cell*, 73, 309–319 (1993)). First, the Ad2 fiber protein attaches the virus to a cell by binding to an as yet unidentified receptor. Then, the penton base binds to $\alpha_v$ integrins, which are a family of a heterodimeric cell-surface receptors that mediate cellular adhesion to the extracellular matrix molecules, as well as other molecules (Hynes, *Cell*, 69, 11–25 (1992)).

The fiber protein is a trimer (Devaux et al., *J. Molec. Biol.*, 215, 567–588 (1990)) consisting of a tail, a shaft, and a knob. The fiber shaft region is composed of repeating 15 amino acid motifs, which are believed to form two alternating β-strands and β-bends (Green et al., *EMBO J.*, 2, 1357–1365 (1983)). The overall length of the fiber shaft region and the number of 15 amino-acid repeats differ between adenoviral serotypes. For example, the Ad2 fiber shaft is 37 nanometers long and contains 22 repeats, whereas the Ad3 fiber is 11 nanometers long and contains 6 repeats. The receptor binding domain of the fiber protein is localized in the knob region encoded by the last 200 amino acids of the protein (Henry et al., *J. Virol.*, 68(8), 5239–5246 (1994)). The regions necessary for trimerization are also located in the knob region of the protein (Henry et al. (1994), supra). A deletion mutant lacking the last 40 amino acids does not trimerize and also does not bind to penton base (Novelli et al., *Virology*, 185, 365–376 (1991)). Thus, trimerization of the fiber protein is necessary for penton base binding. Nuclear localization signals that direct the protein to the nucleus to form viral particles following its synthesis in the cytoplasm are located in the N-terminal region of the protein (Novelli et al. (1991), supra). The fiber, together with the hexon, are the main antigenic determinants of the virus and also determine the serotype specificity of the virus (Watson et al., *J. Gen. Virol.*, 69, 525–535 (1988)).

Recombinant adenoviral vectors have been used for the cell-targeted transfer of one or more recombinant genes to diseased cells or tissue in need of treatment. Such vectors are characterized by the advantage of not requiring host cell proliferation for expression of adenoviral proteins (Horwitz et al., *In Virology*, Raven Press, New York, vol. 2, pp. 1679–1721 (1990); and Berkner, *BioTechniques*, 6, 616 (1988)). Moreover, if the targeted tissue for somatic gene therapy is the lung, these vectors have the added advantage of being normally trophic for the respiratory epithelium (Straus, *In Adenoviruses*, Plenan Press, New York, pp. 451–496 (1984)).

Other advantages of adenoviruses as potential vectors for human gene therapy are: (i) recombination is rarely observed with use of such vectors; (ii) there are no known associations of human malignancies with adenoviral infections despite common human infection with adenoviruses; (iii) the adenoviral genome (which is a linear, double-stranded DNA) can be manipulated to accommodate foreign genes that range in size; (iv) an adenoviral vector does not insert its DNA into the chromosome of a cell, so its effect is impermanent and unlikely to interfere with the cell's normal function; (v) the adenovirus can infect non-dividing or terminally differentiated cells, such as cells in the brain and lungs; and (vi) live adenovirus, having as an essential characteristic the ability to replicate, has been safely used as a human vaccine (Horwitz et al. (1990), supra; Berkner et al. (1988), supra; Straus et al. (1984), supra; Chanock et al., *JAMA*, 195, 151 (1966); Haj-Ahmad et al., *J. Virol.*, 57, 267 (1986); and Ballay et al., *EMBO*, 4, 3861 (1985); PCT patent application WO 94/17832).

A drawback to adenovirus-mediated gene therapy is that significant decreases in gene expression are observed after two weeks following administration of the vector. In many therapeutic applications, the loss of expression requires re-administration of the viral vector. However, following re-administration, neutralizing antibodies are raised against both the fiber and hexon proteins of the viral vector (Wohlfart, *J. Virology*, 62, 2321–2328 (1988); Wohlfart et al., *J. Virology*, 56, 896–903 (1985)). This antibody response against the virus can prevent effective re-administration of the viral vector.

Another drawback of using recombinant adenovirus in gene therapy is that certain cells are not readily amenable to adenovirus-mediated gene delivery. For instance, lymphocytes, which lack the $\alpha_V$ integrin adenoviral receptors, are impaired in the uptake of adenoviruses (Silver et al., *Virology* 165, 377–387 (1988); Horvath et al., *J. Virol.*, 62(1), 341–345 (1988)). This lack of ability to infect all cells has lead researchers to seek out ways to introduce adenovirus into cells that cannot be infected by adenovirus, e.g. due to lack of adenoviral receptors. In particular, the virus can be coupled to a DNA-polylysine complex containing a ligand (e.g., transferring for mammalian cells (e.g., Wagner et al., *Proc. Natl. Acad. Sci.*, 89, 6099–6103 (1992); PCT patent application WO 95/26412). Similarly, adenoviral fiber protein can be sterically blocked with antibodies, and tissue-specific antibodies can be chemically linked to the viral particle (Cotten et al., *Proc. Natl. Acad. Sci. USA*, 89, 6094–6098 (1992)).

However, these approaches are disadvantageous in that they require additional steps that covalently link large molecules, such as polylysine, receptor ligands, and antibodies, to the virus (Cotten (1992), supra; Wagner et al., *Proc. Natl. Acad. Sci.*, 89, 6099–6103 (1992)). This adds to the size of the resultant vector as well as its cost of production. Moreover, the targeted particle complexes are not homogeneous in structure, and their efficiency is sensitive to the relative ratios of viral particles, linking molecules, and targeting molecules used. Thus, this approach for expanding the repertoire of cells amenable to adenoviral-mediated gene therapy is less than optimal.

Recently, the efficiency of adenovirus-mediated gene transfer in vivo to even those cells which adenovirus has been reputed to enter with high efficiency has been called into question (Grubb et al., *Nature*, 371, 802–806 (1994); Dupuit et al., *Human Gene Therapy*, 6, 1185–1193 (1995)). The fiber receptor by means of which adenovirus initially contacts cells has not been identified, and its representation in different tissues has not been examined. It is generally assumed that epithelial cells in the lung and gut produce sufficient levels of the fiber receptor to allow their optimal transduction. However, no studies have confirmed this point to date. In fact, studies have suggested that adenovirus gene delivery to differentiated lung epithelium is less efficient than delivery to proliferating or to undifferentiated cells (Grubb et al., supra; Dupuit et al., supra).

Similarly, adenovirus has been shown to transduce a large number of tissues including lung epithelial cells (Rosenfeld et al., *Cell*, 68, 143–155 (1992)), muscle cells (Quantin et al., *Proc. Natl. Acad. Sci.*, 89, 2581–2584 (1992)), endothelial cells (Lemarchand et al, *Proc. Natl. Acad. Sci.*, 89, 6482–6486 (1992), fibroblasts (Anton et al., *J. Virol.*, 69, 4600–4606 (1995), and neuronal cells (LaSalle et al., *Science*, 259, 988–990 (1993)). However, in many of these studies, very high levels of virus particles have been used to achieve transduction, often exceeding 100 plaque forming units (pfu)/cell, and corresponding to a multiplicity of infection (MOI) of 100. The requirement for a high MOI to achieve transduction is disadvantageous inasmuch as any immune response associated with adenoviral infection necessarily would be exacerbated with use of high doses.

Accordingly, there remains a need for vectors, such as adenoviral vectors, that are capable of infecting cells with a high efficiency, especially at lower MOIs, and that demonstrate an increased host cell range of infectivity. The present invention seeks to overcome at least some of the aforesaid problems of recombinant adenoviral gene therapy. In particular, it is an object of the present invention to provide a vector (such as an adenoviral vector) having a broad host range, and an ability to enter cells with a high efficiency, even at a reduced MOI, thereby reducing the amount of recombinant adenoviral vector administered and any side-effects/complications resulting from such administration. A further object of the present invention is to provide a method of gene therapy involving the use of a homogeneous adenovirus, wherein the viral particle is modified at the level of the adenoviral genome, without the need for additional chemical modifications of viral particles. These and other objects and advantages of the present invention, as well as additional inventive features, will be apparent from the following detailed description.

BRIEF SUMMARY OF THE INVENTION

The present invention provides a chimeric adenoviral coat protein (e.g., a fiber, hexon or penton protein), which differs from the wild-type (i.e., native) fiber protein by the introduction of a nonnative amino acid sequence, preferably at or near the carboxyl terminus. The resultant chimeric adenovirus coat protein is able to direct entry into cells of a vector comprising the coat protein that is more efficient than entry into cells of a vector that is identical except for comprising a wild-type adenovirus coat protein rather than the chimeric adenovirus coat protein. One direct result of this increased efficiency of entry is that the chimeric adenovirus coat protein enables the adenovirus to bind to and enter numerous cell types which adenovirus comprising wild-type coat protein typically cannot enter or can enter with only a low efficiency. The present invention also provides an adenoviral vector that comprises the chimeric adenovirus coat protein, and methods of constructing and using such a vector.

BRIEF DESCRIPTION OF THE FIGURES

FIGS. 2A–B depict attachment of a nucleic acid sequence at the end of the wild-type adenoviral fiber gene (FIG. 2A) to derive a chimeric adenoviral fiber protein (FIG. 2B) comprising a nonnative amino acid sequence at the carboxy terminus. As indicated, the length of the polyA tail, and, consequently, the number of lysines in the resultant protein, can vary.

FIGS. 4A–D depict the oligonucleotides employed for construction of GV10 UTV, i.e., the primers SEQ ID NO:9 (FIG. 4A), SEQ ID NO:10 (FIG. 4B), SEQ ID NO:11 (FIG. 4C), and SEQ ID NO:12 (FIG. 4D).

DETAILED DESCRIPTION OF THE INVENTION

Figure 1:
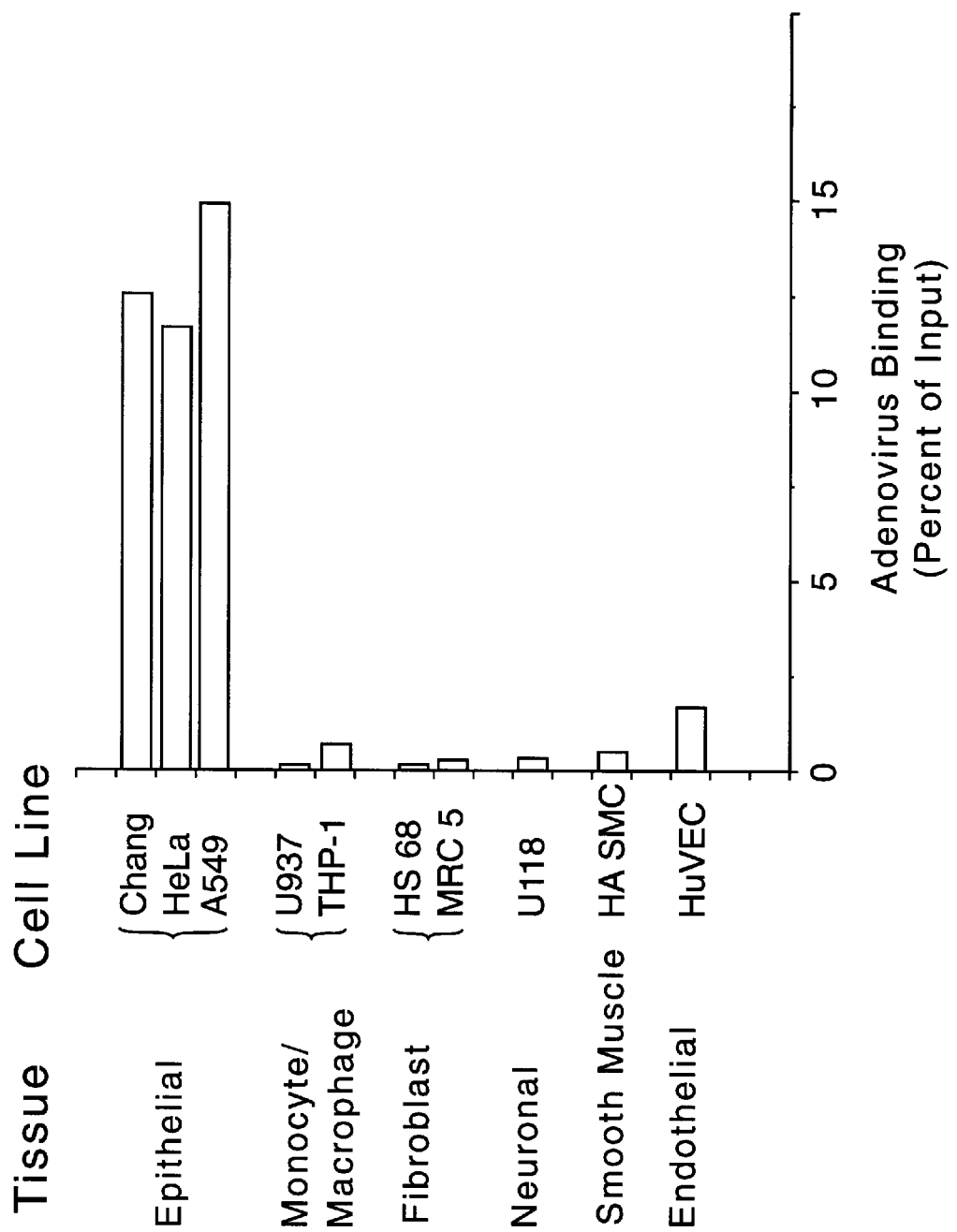
FIG. 1 is a bar graph depicting the binding (percent of input) of wild-type adenovirus to cells derived from different tissues.

The present invention provides, among other things, a recombinant adenovirus comprising a chimeric coat protein, such as a chimeric fiber, penton, and/or hexon protein. The chimeric coat protein comprises a nonnative amino acid sequence, in addition to, or in place of, a native amino acid sequence. This nonnative amino acid sequence allows the chimeric fiber (or a vector comprising the chimeric fiber) to more efficiently bind to and enter cells.

Thus, the present invention provides, a chimeric adenovirus coat protein comprising a nonnative amino acid sequence, wherein the coat protein is able to direct entry into cells of a vector comprising the coat protein that is more efficient than entry into cells of a vector that is identical except for comprising a wild-type adenovirus coat protein rather than the chimeric adenovirus coat protein (i.e., in the absence of the chimeric adenovirus coat protein and in the presence of the wild-type adenovirus coat protein).

Chimeric Coat Protein

A "coat protein" according to the invention preferably comprises a fiber protein (especially an adenoviral fiber protein), a penton protein (especially an adenoviral penton protein), and a hexon protein (especially an adenoviral hexon protein). In particular, a coat protein preferably comprises an adenoviral fiber protein. Any one of the serotypes of human or nonhuman adenovirus can be used as the source of the coat protein gene, optimally, however, the adenovirus is an Ad2 or Ad5 adenovirus.

The coat protein is "chimeric" in that it comprises amino acid residues that are not typically found in the protein as isolated from wild-type adenovirus (i.e., comprising the native protein, or wild-type protein). The coat protein thus comprises a "nonnative amino acid sequence". By "nonnative amino acid sequence" is meant any amino acid sequence that is not found in the native fiber of a given serotype of adenovirus and which preferably is introduced into the fiber protein at the level of gene expression (i.e., by introduction of a "nucleic acid sequence that encodes a nonnative amino acid sequence").

Such a nonnative amino acid sequence comprises an amino acid sequence which imparts upon the resultant chimeric protein an ability to bind to and enter cells by means of a novel cell surface binding site, and/or comprises a spacer sequence (i.e., a sequence incorporated to produce or maintain a certain configuration of the resultant chimeric protein) between native/nonnative, nonnative/nonnative, or a native/native sequence.

A "cell surface binding site" encompasses a receptor (which preferably is a protein, carbohydrate, glycoprotein, or proteoglycan) as well as any oppositely charged molecule (i.e., oppositely charged with respect to the chimeric coat protein) or other type of molecule with which the chimeric coat protein can interact to bind the cell, and thereby promote cell entry. Examples of potential cell surface binding sites include, but are not limited to: heparin and chondroitin sulfate moieties found on glycosaminoglycans; sialic acid moieties found on mucins, glycoproteins, and gangliosides; major histocompatibility complex I (MHC I) glycoproteins; common carbohydrate components found in membrane glycoproteins, including mannose, N-acetyl-galactosamine, N-acetyl-glucosamine, fucose, galactose, and the like. However, a chimeric coat protein according to the invention, and methods of use thereof, is not limited to any particular mechanism of cellular interaction (i.e., interaction with a particular cell surface binding site) and is not to be so construed.

Furthermore, such a cell surface binding site is "novel" inasmuch as the site is one that previously was inaccessible to interaction with an adenoviral coat protein (i.e., wild-type adenoviral coat protein such as fiber protein), or was accessible only at a very low level, as reflected by the reduced efficiency of entry of a wild-type adenoviral coat protein-containing vector as compared with a vector comprising a chimeric adenovirus coat protein such as fiber protein according to the invention. Moreover, the binding site is novel in that it is present on the majority of, if not all, cells, regardless of their origin. This is in contrast to the cellular binding site with which wild-type adenoviral fiber protein is presumed to interact, which ostensibly is present only on a subset of cells, or is only accessible on a subset of cells, as reflected by the reduced efficiency of entry of a wild-type adenoviral fiber-containing vector.

"Efficiency of entry" can be quantitated by several means. In particular, efficiency of entry can be quantitated by introducing a chimeric coat protein into a vector, preferably a viral vector, and monitoring cell entry (e.g., by vector-mediated delivery to a cell of a gene such as a reporter gene) as a function of multiplicity of infection (MOI)). In this case, a reduced MOI required for cell entry of a vector comprising a chimeric adenoviral coat protein as compared with a vector that is identical except for comprising a wild-type adenoviral coat protein rather than said chimeric adenovirus coat protein, indicates "more efficient" entry.

Similarly, efficiency of entry can be quantitated in terms of the ability of vectors containing chimeric or wild-type coat proteins, or the soluble chimeric or wild-type coat proteins themselves, to bind to cells. In this case, increased binding exhibited for the vector containing a chimeric adenoviral coat protein, or the chimeric coat protein itself, as compared with the identical vector containing a wild-type coat protein instead, or the wild-type coat protein itself, is indicative of an increased efficiency of entry, or "more efficient" entry.

A spacer sequence is a sequence that intervenes between the native protein sequence and the nonnative sequence, between a nonnative sequence and another nonnative sequence, or between a native sequence and another native sequence. Such a sequence preferably is incorporated into the protein to ensure that the nonnative sequence comprising the cell surface binding site projects from the three dimensional structure of the chimeric protein (especially the three dimensional structure of the chimeric protein as it exists in nature, i.e., as part of a capsid) in such a fashion so as to be able to interact with and bind to cells.

A nonnative amino acid sequence according to the invention preferably is inserted into or in place of an internal coat protein. Alternately, preferably a nonnative amino acid sequence according to the invention is at or near the C-terminus of a protein. In particular, when a coat protein according to the invention is a fiber protein, desirably a nonnative amino acid sequence is at or near the C-terminus of the protein. When a coat protein according to the invention is a penton or hexon protein, preferably a nonnative amino acid sequence is within an exposed loop of the protein. Thus, desirably a nonnative amino acid sequence is in a region of a coat protein that is capable of interacting with and binding a cell.

Optimally, the nonnative amino acid sequence is linked to the protein by another nonnative amino acid sequence, i.e., by an intervening spacer sequence. An intervening spacer sequence can be of any suitable length, preferably from about 3 to about 30 amino acids, and comprises any amino acids. Optimally, the spacer sequence does not interfere with the functioning of the coat protein in general, and the functioning of the other nonnative amino acid sequence in particular.

The nonnative amino acid sequence, which is not a spacer sequence, can also be of any suitable length, preferably from about 3 to about 30 amino acids. These amino acids preferably are positively charged residues that are capable of binding to negatively charged cell surface binding sites, e.g., desirably the nonnative amino acid sequence comprises amino acids selected from the group consisting of lysine, arginine and histidine. Alternately, these amino acids can be negatively charged residues that are capable of binding to positively charged cell surface binding sites, e.g., desirably the nonnative amino acid sequence comprises amino acids selected from the group consisting of aspartate and glutamate.

Thus, the nonnative amino acid sequence of a coat protein preferably comprises a sequence selected from the group consisting of SEQ ID NO:1 (i.e., Lys Lys Lys Lys Lys Lys Lys Lys), SEQ ID NO:2 (i.e., Arg Arg Arg Arg Arg Arg Arg Arg), and SEQ ID NO:3 (i.e., Xaa Xaa Xaa Xaa Xaa Xaa Xaa Xaa, wherein "Xaa" comprises Lys or Arg), and wherein 1, 2, 3, 4, or 5 residues of the sequence may be deleted at the C-terminus thereof. When the coat protein is a fiber protein, preferably the protein comprises a sequence selected from the group consisting of SEQ ID NO:1, SEQ ID NO:2, SEQ ID NO:3, SEQ ID NO:4 (i.e., Gly Ser Asn Lys Glu Ser Phe Val Leu Lys Lys Lys), and SEQ ID NO:5 (i.e., Ala Gly Ser Asn Lys Asn Lys Glu Ser Phe Val Leu Lys Lys Lys), and wherein 1, 2, 3, 4, or 5 residues of the sequence may be deleted at the C-terminus thereof.

As indicated previously, preferably the nonnative amino acid sequence is introduced at the level of DNA. Accordingly, the invention preferably also provides an isolated and purified nucleic acid encoding a coat protein according to the invention, wherein the nucleic acid sequence that encodes the nonnative amino acid sequence comprises a sequence of SEQ ID NO:6 (i.e., GGA TCC AA), which is located prior to the polyadenylation site. Similarly, the invention preferably provides an isolated and purified nucleic acid comprising a sequence selected from the group consisting of SEQ ID NO:7 (i.e., GGA TCC AAT AAA GAA TCG TTT GTG TTA TGT) and SEQ ID NO:8 (i.e., GCC GGA TCC AAC AAG AAT AAA GAA TCG TTT GTG TTA), as well as conservatively modified variants thereof.

A "conservatively modified variant" is a variation on the nucleic acid sequence that results in a conservative amino acid substitution. A "conservative amino acid substitution" is an amino acid substituted by an alternative amino acid of similar charge density, hydrophilicity/hydrophobicity, size, and/or configuration (e.g., Val for Ile). In comparison, a "nonconservatively modified variant" is a variation on the nucleic acid sequence that results in a nonconservative amino acid substitution. A "nonconservative amino acid substitution" is an amino acid substituted by an alternative amino acid of differing charge density, hydrophilicity/hydrophobicity, size, and/or configuration (e.g., Val for Phe). The means of making such modifications are well known in the art, are described in the Examples which follow, and also can be accomplished by means of commercially available kits and vectors (e.g., New England Biolabs, Inc., Beverly, Mass.; Clontech, Palo Alto, Calif.). Moreover, the means of assessing such substitutions (e.g., in terms of effect on ability to bind and enter cells) are described in the Examples herein.

The means of making such a chimeric coat protein, particularly the means of introducing the sequence at the level of DNA, is well known in the art, is illustrated in FIG. 2 for a representative chimeric protein, and is described in the Examples that follow. Briefly, the method comprises introducing a sequence (preferably the sequence of SEQ ID NO:6 or a conservatively modified variant thereof) into the sequence of the coat protein prior to any stop codon or polyadenylation signal so as to induce a frameshift mutation into the resultant protein, such that the chimeric protein incorporates additional amino acids.

Generally, this can be accomplished by cloning the fiber sequence into a plasmid or some other vector for ease of manipulation of the sequence. Then, restriction sites flanking the sequence at which the frameshift mutation is to be introduced are identified. A double-stranded synthetic oligonucleotide is created from overlapping synthetic single-stranded sense and antisense oligonucleotides (e.g., from the sense and antisense oligonucleotides, respectively, TAT GGA GGA TCC AAT AAA GAA TCG TTT GTG TTA TGT TTC AAC GTG TTT ATT TTT C [SEQ ID NO:9] and AAT TGA AAA ATA AAC ACG TTG AAA CAT AAC ACA AAC GAT TCT TTA TTG GAT CCT CCA [SEQ ID NO:10], as illustrated in FIG. 4) such that the double-stranded oligonucleotide incorporates the restriction sites flanking the target sequence. The plasmid or other vector is cleaved with the restriction enzymes, and the oligonucleotide sequence having compatible cohesive ends is ligated in to the plasmid or other vector, to replace the wild-type DNA. Other means of in vitro site-directed mutagenesis such as are known to those skilled in the art, and can be accomplished (in particular, using PCR), for instance, by means of commercially available kits, can be used to introduce the mutated sequence into the coat protein coding sequence.

Once the sequence is introduced into the chimeric coat protein, the nucleic acid fragment encoding the sequence can be isolated, e.g., by PCR amplification using 5' and 3' primers. For instance, with respect to a chimeric fiber protein, the fragment can be isolated by PCR using the primer TCCC CCCGGG TCTAGA TTA GGA TCC TTC TTG GGC AAT GTA TGA [SEQ ID NO:11], and the primer CGT GTA TCC ATA TGA CAC AGA [SEQ ID NO:12], as illustrated in FIG. 4. Use of these primers in this fashion results in an amplified chimeric fiber-containing fragment that is flanked by restriction sites (i.e., in this case NdeI and BamHI sites) that can be used for convenient subcloning of the fragment. Other means of generating a chimeric coat protein also can be employed.

Thus, the frameshift mutation can be introduced into any part of a coat protein coding sequence. With respect to SEQ ID NO:6, for instance, this sequence can be placed at the region of the coat protein gene that codes for the C-terminus of the protein (i.e., can be added immediately prior to the TAA stop codon), or can be placed earlier into the coding region, such as between codons coding for Ala (i.e., A) and Gln (i.e., Q) to produce the aforementioned coding sequence of SEQ ID NO:8, which encodes a chimeric protein comprising the sequence of SEQ ID NO:5. Similarly, this approach can be employed to introduce a frameshift even earlier in the coding sequence, e.g., either inserted into or in place of an internal (i.e., native) coat protein sequence.

Moreover, the double-stranded oligonucleotide can also incorporate a further restriction site that also can be employed in manipulating the sequence. For instance, the sequence of SEQ ID NO:6 introduced in the vector comprises a modified BamHI site, i.e., the site is "modified" in that it adds additional nucleotides onto the palindromic recognition sequence. This sequence also can be synthesized to comprise any other restriction site convenient for DNA manipulations. When incorporated into the coat protein coding sequence, the sequence not only introduces a frame shift mutation, but also can be used to introduce other coding sequences into the coat protein gene. In particular, the coding sequences introduced in this fashion can comprise codons for lysine, arginine and histidine, or codons for aspartate and glutamate, either alone, or in any combination. Furthermore, a new translation stop codon can follow these codons for the amino acids, allowing a chimeric protein to be produced that only incorporates a given number of additional amino acids in the nonnative amino acid sequence. The codons for the amino acids and the translation stop codon can be introduced into the frameshift mutation-inducing novel restriction site incorporated into the coat protein by synthesizing oligonucleotides comprising these sequences that are flanked by the restriction site as previously described (e.g., that comprise 5' and 3' BamHI sites), or by other such means that are known to those skilled in the art.

The size of the DNA used to replace the native receptor binding sequence may be constrained, for example, by impeded folding of the fiber or improper assembly of the penton base/fiber complex. DNA encoding the aforementioned amino acid sequences (e.g., lysine, arginine, histidine, aspartate, glutamate, and the like) is preferred for insertion into the fiber gene sequence in which the native receptor binding sequence has been deleted or otherwise mutated. Moreover, other DNA sequences, such as those that encode amino acids for incorporation into spacer sequences, preferably are used to replace the native coat protein coding sequence.

Vector Comprising a Chimeric Coat Protein

A "vector" according to the invention is a vehicle for gene transfer as that term is understood by those skilled in the art. Four types of vectors encompassed by the invention are plasmids, phages, viruses, and liposomes. Plasmids, phages, and viruses can be transferred to a cell in their nucleic acid form, and liposomes can be employed to transfer nucleic acids. Hence, the vectors that can be employed for gene transfer include those referred to herein as "transfer vectors".

Preferably, a vector according to the invention is a virus, especially a virus selected from the group consisting of nonenveloped viruses, i.e., nonenveloped RNA or DNA viruses. Also, a virus can be selected from the group consisting of enveloped viruses, i.e., enveloped RNA or DNA viruses. Such viruses preferably comprise a coat protein. Desirably, the viral coat protein is one that projects outward from the capsid such that it is able to interact with cells. In the case of enveloped RNA or DNA viruses, preferably the coat protein is in fact a lipid envelope glycoprotein (i.e., a so-called spike or peplomer).

In particular, preferably a vector is a nonenveloped virus (i.e., either a RNA or DNA virus) from the family Hepadnaviridae, Parvoviridae, Papovaviridae, Adenoviridae, or Picornaviridae. A preferred nonenveloped virus according to the invention is a virus of the family Hepadnaviridae, especially of the genus Hepadnavirus. A virus of the family Parvoviridae desirably is of the genus Parvovirus (e.g., parvoviruses of mammals and birds) or Dependovirus (e.g., adeno-associated viruses (AAVs)). A virus of the family Papovaviridae preferably is of the subfamily Papillomavirinae (e.g., the papillomaviruses including, but not limited to, human papillomaviruses (HPV) 1-48) or the subfamily Polyomavirinae (e.g., the polyomaviruses including, but not limited to, JC, SV40 and BK virus). A virus of the family Adenoviridae desirably is of the genus Mastadenovirus (e.g., mammalian adenoviruses) or Aviadenovirus (e.g., avian adenoviruses). A virus of the family Picornaviridae is preferably a hepatitis A virus (HAV), hepatitis B virus (HBV), or a non-A or non-B hepatitis virus.

Similarly, a vector can be an enveloped virus from the family Herpesviridae or Retroviridae, or can be a Sindbis virus. A preferred enveloped virus according to the invention is a virus of the family Herpesviridae, especially of the subfamily or genus Alphaherpesvirinae (e.g., the herpes simplex-like viruses), Simplexvirus (e.g., herpes simplex-like viruses), Varicellavirus (e.g., varicella and pseudorabies-like viruses), Betaherpesvirinae (e.g., the cytomegaloviruses), Cytomegalovirus (e.g., the human cytomegaloviruses), Gammaherpesvirinae (e.g., the lymphocyte-associated viruses), and Lymphocryptovirus (e.g., EB-like viruses).

Another preferred enveloped virus is a RNA virus of the family Retroviridae (i.e., preferably is a retrovirus), particularly a virus of the genus or subfamily Oncovirinae, spumavirinae, Spumavirus, Lentivirinae, and Lentivirus. A RNA virus of the subfamily Oncovirinae is desirably a human T-lymphotropic virus type 1 or 2 (i.e., HTLV-1 or HTLV-2) or bovine leukemia virus (BLV), an avian leukosis-sarcoma virus (e.g., Rous sarcoma virus (RSV), avian myeloblastosis virus (AMV), avian erythroblastosis virus (AEV), Rous-associated virus (RAV)-1 to 50, RAV-0), a mammalian C-type virus (e.g., Moloney murine leukemia virus (MuLV), Harvey murine sarcoma virus (HaMSV), Abelson murine leukemia virus (A-MuLV), AKR-MuLV, feline leukemia virus (FeLV), simian sarcoma virus, reticuloendotheliosis virus (REV), spleen necrosis virus (SNV)), a B-type virus (e.g., mouse mammary tumor virus (MMTV)), or a D-type virus (e.g., Mason-Pfizer monkey virus (MPMV), "SAIDS" viruses). A RNA virus of the subfamily Lentivirus is desirably a human immunodeficiency virus type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. The acronym "HIV" or terms "AIDS virus" or "human immunodeficiency virus" are used herein to refer to these HIV viruses, and HIV-related and -associated viruses, generically. Moreover, a RNA virus of the subfamily Lentivirus preferably is a Visna/maedi virus (e.g., such as infect sheep), a feline immunodeficiency virus (FIV), bovine lentivirus, simian immunodeficiency virus (SIV), an equine infectious anemia virus (EIAV), or a caprine arthritis-encephalitis virus (CAEV).

An especially preferred vector according to the invention is an adenoviral vector (i.e., a viral vector of the family Adenoviridae, optimally of the genus Mastadenovirus). Desirably such a vector is an Ad2 or Ad5 vector, although other serotype adenoviral vectors can be employed. The adenoviral vector employed for gene transfer can be wild-type (i.e., replication competent). Alternately, the adenoviral vector can comprise genetic material with at least one modification therein, which can render the virus replication deficient. The modification to the adenoviral genome can include, but is not limited to, addition of a DNA segment, rearrangement of a DNA segment, deletion of a DNA segment, replacement of a DNA segment, or introduction of a DNA lesion. A DNA segment can be as small as one nucleotide and as large as 36 kilobase pairs (i.e., the approximate size of the adenoviral genome) or, alternatively, can equal the maximum amount which can be packaged into an adenoviral virion (i.e., about 38 kb). Preferred modifications to the adenoviral genome include modifications in the E1, E2, E3 or E4 region. Similarly, an adenoviral vector can be a cointegrate, i.e., a ligation of adenoviral sequences, with other sequences, such as other virus or plasmid sequences.

In terms of a viral vector (e.g., particularly a replication deficient adenoviral vector), such a vector can comprise either complete capsids (i.e., including a viral genome such as an adenoviral genome) or empty capsids (i.e., in which a viral genome is lacking, or is degraded, e.g., by physical or chemical means). Along the same lines, since methods are available for transferring viruses, plasmids, and phages in the form of their nucleic acid sequences (i.e., RNA or DNA), a vector (i.e., a transfer vector) similarly can comprise RNA or DNA, in the absence of any associated protein such as capsid protein, and in the absence of any envelope lipid. Similarly, since liposomes effect cell entry by fusing with cell membranes, a transfer vector can comprise liposomes (e.g., such as are commercially available, for instance, from Life Technologies, Bethesda, Md.), with constitutive nucleic acids encoding the coat protein. Thus, according to the invention whereas a vector "comprises" a chimeric adenoviral coat protein, a transfer vector "encodes" a chimeric adenoviral coat protein; liposome transfer vectors in particular "encode" in the sense that they contain nucleic acids which, in fact, encode the protein.

A vector according to the invention can comprise additional sequences and mutations, e.g., some within the coat protein itself. For instance, a vector according to the invention further preferably comprises a nucleic acid comprising a passenger gene.

A "nucleic acid" is a polynucleotide (DNA or RNA). A "gene" is any nucleic acid sequence coding for a protein or a nascent RNA molecule. A "passenger gene" is any gene which is not typically present in and is subcloned into a vector (e.g., a transfer vector) according to the present invention, and which upon introduction into a host cell is accompanied by a discernible change in the intracellular environment (e.g., by an increased level of deoxyribonucleic acid (DNA), ribonucleic acid (RNA), peptide or protein, or by an altered rate of production or degradation thereof). A "gene product" is either an as yet untranslated RNA molecule transcribed from a given gene or coding sequence (e.g., mRNA or antisense RNA) or the polypeptide chain (i.e., protein or peptide) translated from the mRNA molecule transcribed from the given gene or coding sequence. Whereas a gene comprises coding sequences plus any non-coding sequences, a "coding sequence" does not include any non-coding (e.g., regulatory) DNA. A gene or coding sequence is "recombinant" if the sequence of bases along the molecule has been altered from the sequence in which the gene or coding sequence is typically found in nature, or if the sequence of bases is not typically found in nature. According to this invention, a gene or coding sequence can be wholly or partially synthetically made, can comprise genomic or complementary DNA (cDNA) sequences, and can be provided in the form of either DNA or RNA.

Non-coding sequences or regulatory sequences include promoter sequences. A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription is also termed a "silencer". Enhancers differ from DNA-binding sites for sequence-specific DNA binding proteins found only in the promoter (which are also termed "promoter elements") in that enhancers can function in either orientation, and over distances of up to several kilobase pairs, even from a position downstream of a transcribed region. According to the invention, a coding sequence is "operably linked" to a promoter (e.g., when both the coding sequence and the promoter constitute a passenger gene) when the promoter is capable of directing transcription of that coding sequence.

Accordingly, a "passenger gene" can be any gene, and desirably is either a therapeutic gene or a reporter gene. Preferably a passenger gene is capable of being expressed in a cell in which the vector has been internalized. For instance, the passenger gene can comprise a reporter gene, or a nucleic acid sequence which encodes a protein that can in some fashion be detected in a cell. The passenger gene also can comprise a therapeutic gene, for instance, a therapeutic gene which exerts its effect at the level of RNA or protein. For instance, a protein encoded by a transferred therapeutic gene can be employed in the treatment of an inherited disease, such as, e.g., the cystic fibrosis transmembrane conductance regulator cDNA for the treatment of cystic fibrosis. The protein encoded by the therapeutic gene may exert its therapeutic effect by resulting in cell killing. For instance, expression of the gene in itself may lead to cell killing, as with expression of the diphtheria toxin A gene, or the expression of the gene may render cells selectively sensitive to the killing action of certain drugs, e.g., expression of the HSV thymidine kinase gene renders cells sensitive to antiviral compounds including acyclovir, gancyclovir and FIAU (1-(2-deoxy-2-fluoro-$\beta$-D-arabinofuranosil)-5-iodouracil).

Moreover, the therapeutic gene can exert its effect at the level of RNA, for instance, by encoding an antisense message or ribozyme, a protein which affects splicing or 3' processing (e.g., polyadenylation), or can encode a protein which acts by affecting the level of expression of another gene within the cell (i.e., where gene expression is broadly considered to include all steps from initiation of transcription through production of a processed protein), perhaps, among other things, by mediating an altered rate of mRNA accumulation, an alteration of mRNA transport, and/or a change in post-transcriptional regulation. Accordingly, the use of the term "therapeutic gene" is intended to encompass these and any other embodiments of that which is more commonly referred to as gene therapy and is known to those of skill in the art. Similarly, the recombinant adenovirus can be used for gene therapy or to study the effects of expression of the gene in a given cell or tissue in vitro or in vivo.

The recombinant adenovirus comprising a chimeric coat protein such as a fiber protein and the recombinant adenovirus that additionally comprises a passenger gene or genes capable of being expressed in a particular cell can be generated by use of a transfer vector, preferably a viral or plasmid transfer vector, in accordance with the present invention. Such a transfer vector preferably comprises a chimeric adenoviral coat protein gene sequence as previously described. The chimeric coat protein gene sequence comprises a nonnative sequence in place of the native sequence, which has been deleted, or in addition to the native sequence.

A recombinant chimeric coat protein gene sequence (such as a fiber gene sequence) can be moved from an adenoviral transfer vector into baculovirus or a suitable prokaryotic or eukaryotic expression vector for expression and evaluation of receptor or protein specificity and avidity, trimerization potential, penton base binding, and other biochemical characteristics.

Accordingly, the present invention also provides recombinant baculoviral and prokaryotic and eukaryotic expression vectors comprising a chimeric adenoviral coat protein gene sequence (preferably a fiber gene sequence), which also are "transfer vectors" as defined herein. The chimeric coat protein gene sequence (e.g., fiber gene sequence) includes a nonnative sequence in addition to or in place of a native amino acid sequence, and which enables the resultant chimeric coat protein (e.g., fiber protein) to bind to a binding site other than a binding site bound by the native sequence. By moving the chimeric gene from an adenoviral vector to baculovirus or a prokaryotic or eukaryotic expression vector, high protein expression is achievable (approximately 5–50% of the total protein being the chimeric fiber).

A vector according to the invention further can comprise, either within, in place of, or outside of the coding sequence of a coat protein additional sequences that impact upon the ability of a coat protein such as fiber protein to trimerize, or comprise a protease recognition sequence. A sequence that impacts upon the ability to trimerize is one or more sequences that enable trimerization of a chimeric coat protein that is a fiber protein. A sequence that comprises a protease recognition sequence is a sequence that can be cleaved by a protease, thereby effecting removal of the chimeric coat protein (or a portion thereof) and attachment of the recombinant adenovirus to a cell by means of another coat protein. When employed with a coat protein that is a fiber protein, the protease recognition site preferably does not affect fiber trimerization or receptor specificity of the fiber protein. For instance, in one embodiment of the present invention, preferably the fiber protein, or a portion thereof, is deleted in by means of a protease recognition sequence, and then the novel cell surface binding site is incorporated into either the penton base or hexon coat protein, preferably with use of a spacer sequence as previously described.

Figure 3:
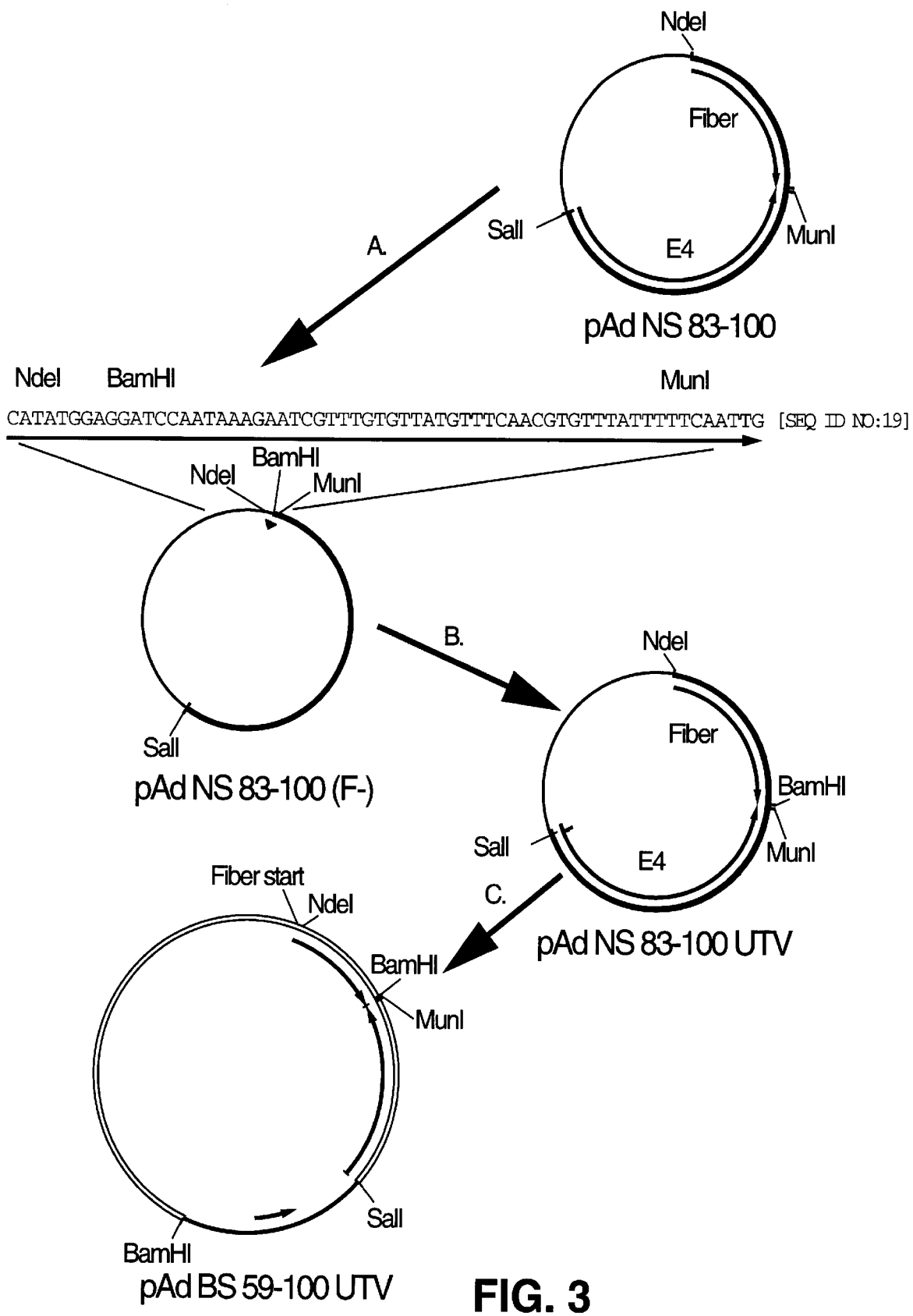
FIG. 3 is a schematic diagram depicting the construction of the adenovirus transfer vector containing chimeric fiber protein pAd BS 59-100 UTV by way of intermediary transfer vectors. In particular, pAd NS 83-100 is used to derive fiber minus (i.e., F⁻) pAd NS 83-100 (path A), pAd NS 83 100 (F⁻) is used to derive pAd NS 83-100 UTV (path B), and pAd NS 83-100 UTV is used to derive pAd BS 59-100 UTV (path C).

In terms of the production of vectors and transfer vectors according to the invention, transfer vectors are constructed using standard molecular and genetic techniques such as are known to those skilled in the art. Vectors (e.g., virions or virus particles) are produced using viral vectors. For instance, a viral vector comprising a chimeric coat protein according to the invention can be constructed by providing to a cell that does not comprise any E4 complementing sequences: (1) a linear vector comprising the chimeric fiber and the wild-type E4 gene, and (2) a linear vector that is E4$^-$, as illustrated in FIG. 3. As described in the Examples which follow, this methodology results in recombination between the sequences, generating a vector that comprises a portion of the initial E4$^-$ vector and a portion of the E4$^+$ vector, particularly the region comprising the chimeric fiber sequences.

Similarly, the fiber chimera-containing particles are produced in standard cell lines, e.g., those currently used for adenoviral vectors. Following production and purification, the particles in which fiber is to be deleted are rendered fiberless through digestion of the particles with a sequence-specific protease, which cleaves the fiber proteins and releases them from the viral particles to generate fiberless particles. For example, thrombin recognizes and cleaves at known amino acid sequences that can be incorporated into the vector (Stenflo et al., *J. Biol. Chem.*, 257, 12280–12290 (1982)). Similarly, deletion mutants lacking the fiber gene can be employed in vector construction, e.g., H2dl802, H2dl807, and H2dl1021 (Falgout et al., *J. Virol.*, 62, 622–625 (1988). These fiberless particles have been shown to be stable and capable of binding and infecting cells (Falgout et al., supra). These resultant particles then can be targeted to specific tissues via the penton base or other coat protein, preferably such other coat protein that comprises one or more nonnative amino acid sequences according to the invention.

Alternately, recombinant adenovirus comprising chimeric fiber protein having further modifications can be produced by the removal of the native knob region, which comprises receptor-binding and trimerization domains, of the fiber protein and its replacement with a nonnative trimerization domain (Peteranderl et al., *Biochemistry*, 31, 12272–12276 (1992)) and a nonnative amino acid sequence according to the invention. A recombinant adenovirus comprising a chimeric fiber protein also can be produced by point mutation in the knob region and the isolation of clones that are capable of trimerization. In either case, and also with respect to the removal and replacement of the native receptor-specific binding sequence as described above, new protein binding domains can be added onto the C-terminus of the fiber protein or into exposed loops of the fiber protein by inserting one or more copies of the nucleic acid sequence encoding the nonnative amino acid sequence into the appropriate position. Preferably, such a fiber protein is able to trimerize, so that it is able to bind to penton base protein.

The method described above for generating chimeric fiber protein also can be used to make other chimeric coat proteins, e.g., chimeric hexon or penton protein.

Illustrative Uses

The present invention provides a chimeric protein that is able to bind to cells and mediate entry into cells with high efficiency, as well as vectors and transfer vectors comprising same. The chimeric coat protein itself has multiple uses, e.g., as a tool for studies in vitro of adenovirus binding to cells (e.g., by Scatchard analysis as shown previously by Wickham et al. (1993), supra), to block binding of adenovirus to receptors in vitro (e.g., by using antibodies, peptides, and enzymes, as described in the Examples), and to protect against adenoviral infection in vivo by competing for binding to the binding site by which adenovirus effects cell entry.

A vector comprising a chimeric coat protein also can be used in strain generation and as a means of making new vectors. For instance, the nonnative amino acid sequence can bind to nucleic acids, and can be introduced intracellularly as a means of generating new vectors via recombination. Similarly, a vector can be used in gene therapy. For instance, a vector of the present invention can be used to treat any one of a number of diseases by delivering to targeted cells corrective DNA, i.e., DNA encoding a function that is either absent or impaired, or a discrete killing agent, e.g., DNA encoding a cytotoxin that, for example, is active only intracellularly. Diseases that are candidates for such treatment include, for example, cancer, e.g., melanoma, glioma or lung cancers; genetic disorders, e.g., cystic fibrosis, hemophilia or muscular dystrophy; pathogenic infections, e.g., human immunodeficiency virus, tuberculosis or hepatitis; heart disease, e.g., preventing restenosis following angioplasty or promoting angiogenesis to reperfuse necrotic tissue; and autoimmune disorders, e.g., Crohn's disease, colitis or rheumatoid arthritis.

In particular, gene therapy can be carried out in the treatment of diseases, disorders, or conditions associated with different tissues that ostensibly lack high levels of the receptor to which wild-type adenovirus fiber protein binds, and thus for which current adenoviral-mediated approaches to gene therapy are less than optimal (e.g., for delivery to monocyte/macrophages, fibroblasts, neuronal, smooth muscle, and epithelial cells). Tissues comprised of these cells (and diseases, disorders, or conditions associated therewith) include, but are not limited to: endothelia (e.g., angiogenesis, restenosis, inflammation, and tumors); neuronal tissue (e.g., tumors and Alzheimer's disease); epithelium (e.g., disorders of the skin, cornea, intestine, and lung); hematopoietic cells (e.g., human immunodeficiency virus (HIV-1, HIV-2), cancers, and anemias); smooth muscle (e.g., restenosis); and fibroblasts (e.g., inflammation).

These aforementioned illustrative uses are by no means comprehensive, and it is intended that the present invention encompasses such further uses which flow from, but are not explicitly recited, in the disclosure herein. Similarly, there are numerous advantages associated with the use of the various aspects of the present invention.

For instance, use of a universal targeting vector according to the invention is advantageous inasmuch as: (1) the vector can potentially be used for all cells and tissues; (2) only one vector is required for use in all cell lines, there is no need for co-transfecting an independent vector; (3) the vector is capable of effecting gene delivery with an efficiency that is increased over that observed for vectors comprising wild-type fiber protein; (4) the vector, unlike prior vectors, does not target specific cells, but instead increases transduction efficiency in what appears to be a global fashion; (5) the vector is capable of mediating gene transfer when employed at a reduced dose (i.e., multiplicity of infection (MOI)) as compared with vector comprising wild-type fiber protein, and thus likely reduces the dosage-related drawbacks that accompany currently available adenoviral vectors; and (6) the vector can be propagated and maintained using currently available cell lines.

The ability of a universal targeting vector such as a universal targeting adenovirus vector to potentially bind to and enter all or most tissues has several advantages. These advantages include increased gene delivery efficiency to multiple tissues, the availability of a single vector capable of delivering genes to all tissues, and simplified production of necessary components for gene delivery. Moreover, such a universal targeting vector comprises a potential to deliver exogenous DNA into cells by "piggy backing" the DNA on the vector by means of a protein/DNA interaction.

Further potential advantages of such a universal targeting vector include a substantially increased efficiency of delivery (e.g., increased by 10- to 100-fold) into cells expressing low levels of fiber receptor to which wild-type fiber protein binds, as well as increased efficiency into cells or tissues expressing fiber receptor to which wild-type fiber binds. Moreover the reduced dosage at which the vectors are employed should result in a decrease in adenovirus-associated inflammation, the humoral response to adenovirus, and the cytotoxic T-lymphocyte response to adenovirus.

Furthermore, the vector is advantageous in that it can be isolated and purified by conventional means. Since changes in the vector are made at the genome level, there are no cumbersome and costly post-production modifications required, as are associated with other vectors (see, e.g., Cotten et al., supra; Wagner et al., supra). Similarly, special receptor-expressing cells lines are not required. A UTV vector can be propagated to similar titers as a wild-type vector lacking the fiber modification.

Means of Administration

The vectors and transfer vectors of the present invention can be employed to contact cells either in vitro or in vivo. According to the invention "contacting" comprises any means by which a vector is introduced intracellularly; the method is not dependent on any particular means of introduction and is not to be so construed. Means of introduction are well known to those skilled in the art, and also are exemplified herein.

Accordingly, introduction can be effected, for instance, either in vitro (e.g., in an ex vivo type method of gene therapy or in tissue culture studies) or in vivo by electroporation, transformation, transduction, conjugation or triparental mating, (co-)transfection, (co-)infection, membrane fusion with cationic lipids, high velocity bombardment with DNA-coated microprojectiles, incubation with calcium phosphate-DNA precipitate, direct microinjection into single cells, and the like. Similarly, the vectors can be introduced by means of cationic lipids, e.g., liposomes. Such liposomes are commercially available (e.g., Lipofectin®, Lipofectamine™, and the like, supplied by Life Technologies, Gibco BRL, Gaithersburg, Md.). Moreover, liposomes having increased transfer capacity and/or reduced toxicity in vivo (see, e.g., PCT patent application WO 95/21259) can be employed in the present invention. Other methods also are available and are known to those skilled in the art.

According to the invention, a "host" (and thus a "cell" from a host) encompasses any host into which a vector of the invention can be introduced, and thus encompasses an animal, including, but not limited to, an amphibian, bird, fish, insect, reptile, or mammal. Optimally a host is a mammal, for instance, rodent, primate (such as chimpanzee, monkey, ape, gorilla, orangutan, or gibbon), feline, canine, ungulate (such as ruminant or swine), as well as, in particular, human.

Inasmuch as a universal targeting vector ostensibly enters all cells, a cell can be any cell into which such a vector can enter. In particular, a universal targeting vector can be employed for gene transfer to a cell that expresses low or undetectable levels of fiber receptor, including, but not limited to, an endothelial, smooth muscle, neuronal, hematopoietic, or fibroblast cell.

One skilled in the art will appreciate that suitable methods of administering a vector (particularly an adenoviral vector) of the present invention to an animal for purposes of gene therapy (see, for example, Rosenfeld et al., Science, 252, 431–434 (1991); Jaffe et al., Clin. Res., 39(2), 302A (1991); Rosenfeld et al., Clin. Res., 39(2), 311A (1991); Berkner, BioTechniques, 6, 616–629 (1988)), chemotherapy, and vaccination are available, and, although more than one route can be used for administration, a particular route can provide a more immediate and more effective reaction than another route. Pharmaceutically acceptable excipients also are well-known to those who are skilled in the art, and are readily available. The choice of excipient will be determined in part by the particular method used to administer the recombinant vector. Accordingly, there is a wide variety of suitable formulations for use in the context of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

A vector or transfer vector of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, a vector or transfer vector of the present invention can be made into suppositories by mixing with a variety of bases such as emulsifying bases or water-soluble bases.

Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the gene of interest, the composition employed, the method of administration, and the particular site and organism being treated. However, the dose should be sufficient to effect a therapeutic response.

As previously indicated, a vector or a transfer vector of the present invention also has utility in vitro. Such a vector can be used as a research tool in the study of adenoviral attachment and infection of cells and in a method of assaying binding site-ligand interaction. Similarly, the recombinant coat protein comprising a nonnative amino acid sequence in addition to or in place of a native receptor binding sequence can be used in receptor-ligand assays and as adhesion proteins in vitro or in vivo, for example.

The following examples further illustrate the present invention and, of course, should not be construed as in any way limiting its scope.

EXAMPLE 1

This example describes an investigation of the levels of adenovirus receptor in different cells, as determined by the ability of wild-type adenovirus to bind to the cells.

For these experiments, the ability of adenovirus comprising wild-type fiber to bind to cells derived from various tissues was assessed. Adenovirus particles of an Ad5 strain were labeled with [$^3$H]-thymidine as previously described (see, e.g., Wickham et al., Cell, 73, 309–319 (1993)). Subsaturating levels of thymidine-labeled adenovirus were added to 200 $\mu$l of $10^6$ cells preincubated about 30 to 60 minutes with or without 20 $\mu$g/ml of soluble fiber protein. The cells were incubated with the virus for 1 hour at 4° C. and then washed 3 times with cold phosphate buffered saline (PBS). The remaining cell-associated counts were measured in a scintillation counter. Specific binding was measured by subtracting the cell-associated counts (i.e., counts per minute (cpm)) in the presence of fiber from the cell-associated counts in the absence of fiber. Binding in the presence of fiber was never more than 2% of the total input of radioactive virus particles. Results were obtained as the average of triplicate measurements.

As illustrated in FIG. 1, a substantial number of the cells derived from different tissues expressed little or no fiber receptor, as indicated by a relative inability of wild-type adenovirus to bound to these cells. Cells of epithelial origin (i.e., "receptor-plus" cells including Chang, HeLa, and A549 cells) bound high levels of adenovirus. In comparison, non-epithelial cells (i.e., "receptor-minus" cells such as monocyte/macrophages, fibroblasts, neuronal, smooth muscle, and epithelial cells) exhibited about 10-fold or more reductions in virus binding as compared to epithelial-like cells.

These results confirm the previously unrecognized relative inability of adenovirus to bind to and hence enter receptor-minus non-epithelial cells, as compared with receptor-plus epithelial cells. Presumably this inability is due to the low representation of receptors for wild-type adenoviral fiber protein on these cells.

EXAMPLE 2

This example describes the construction of an adenoviral vector comprising a chimeric coat protein, particularly a chimeric adenoviral fiber protein.

To overcome the transduction limitation imposed by the presence of only a limited number of fiber receptors on clinically relevant tissues such as non-epithelial tissue, a modified adenovirus vector was constructed as depicted in FIGS. 2A and 2B to derive a vector that is referred to herein as a "universal transfer vector", or UTV. In particular, a frameshift mutation was created in a gene encoding an adenoviral coat protein, in this case, in the fiber gene. In wild-type adenovirus, the unmodified fiber gene contains a nested translational stop signal (TAA) and transcriptional polyadenylation signal (AATAAA). The polyadenylation signal directs the addition of a polyA tail onto the 3' end of the transcript. The polyA tail typically comprises anywhere from about 20 to about 200 nucleotides. Following transcription and exit from the nucleus, the TAA stop signal directs termination of translation by the ribosome.

In comparison, the modified fiber gene of a UTV vector lacks an in-frame translational "stop" signal. Following normal transcription and addition of the polyA extension onto the mRNA, in the absence of the stop codon, the ribosome continues translation of the transcript into the polyA region. Inasmuch as the codon AAA codes for the amino acid lysine, the resultant chimeric fiber gene translation product produced by a UTV contains an addition of a string of polylysine residues at the C-terminus, i.e., Lys Lys Lys Lys Lys Lys Lys Lys [SEQ ID NO:1]. It is possible that a cellular process acts to limit the length of the polylysine string, since the polylysine residues typically comprise from about 3 to about 30 residues in the chimeric fiber protein. Whatever the case, however, the polylysine protein modification, as well as further modifications described herein, allows the UTV to efficiently attach to cells lacking high levels of the receptor for wild-type adenoviral fiber protein (i.e., receptor-minus cells).

In terms of vector construction and characterization, standard molecular and genetic techniques, such as the generation of strains, plasmids, and viruses, gel electrophoresis, DNA manipulations including plasmid isolation, DNA cloning and sequencing, Western blot assays, and the like, were performed such as are known to those skilled in the art, and as are described in detail in standard laboratory manuals (e.g., Maniatis et al., *Molecular Cloning: A Laboratory Manual*, 2nd ed. (Cold Spring Harbor, N.Y., 1992); Ausubel et al., *Current Protocols in Molecular Biology*, (1987)). Restriction enzymes and other enzymes used for molecular manipulations were purchased from commercial sources (e.g., Boehringer Mannheim, Inc., Indianapolis, Ind.; New England Biolabs, Beverly, Mass.; Bethesda Research Laboratories, Bethesda, Md.), and were used according to the recommendations of the manufacturer. Cells employed for experiments (e.g., cells of the transformed human embryonic kidney cell line 293 (i.e., CRL 1573 cells) and other cells supplied by American Type Culture Collection) were cultured and maintained using standard sterile culture reagents, media and techniques, as previously described (Erzerum et al., *Nucleic Acids Research*, 21, 1607–1612 (1993)).

Accordingly, the frameshift mutation of the fiber stop codon was created by introducing a modified BamHI site (i.e., GGATCCAA [SEQ ID NO:6]) into an adenoviral transfer vector. This was done as illustrated in FIG. 3 by removing the NdeI-MunI fiber gene-containing fragment from the plasmid pAd NS 83-100. pAd NS 83-100 contains adenovirus sequences comprising from the NdeI to SalI restriction sites, which spans the 83-100 map unit region of the Ad5 genome. The NdeI-MunI fragment was replaced with a synthetic oligonucleotide comprising the modified BamHI site, which was flanked by a 5' NdeI site and a 3' MunI site to facilitate cloning. The double-stranded synthetic oligonucleotide fragment was created from the overlapping synthetic single-stranded sense and antisense oligonucleotides, i.e., respectively, the primer TAT GGA GGA TCC AAT AAA GAA TCG TTT GTG TTA TGT TTC AAC GTG TTT ATT TTT C [SEQ ID NO:9], and the primer AAT TGA AAA ATA AAC ACG TTG AAA CAT AAC ACA AAC GAT TCT TTA TTG GAT CCT CCA [SEQ ID NO:10], as illustrated in FIGS. 4A and 4B, respectively.

The resultant vector, pAd NS 83-100, lacks all but the first 50 base pairs of the coding sequence for the fiber gene (i.e., is "fiber-minus"). The vector furthermore contains the entire adenovirus E4 coding sequence. The vector retains the "AATAAA" polyadenylation signal included in the synthetic NdeI/MunI oligonucleotide and also incorporates the modified BamHI restriction site.

The mutated fiber gene was incorporated into the fiber-minus pAd NS 83-100 plasmid using synthetic sense and antisense oligonucleotide primers to amplify the fiber gene with use of the polymerase chain reaction (PCR) while incorporating a modified BamHI site following the last codon of the fiber gene to create the mutant fiber gene. This incorporated modified BamHI site also serves to code for the amino acids glycine and serine, resulting in a chimeric nucleic acid sequence of GGA TCC AAT AAA GAA TCG TTT GTG TTA TGT [SEQ ID NO:7]. The modified fiber gene codes for an extension to the resultant chimeric fiber protein of Gly Ser Asn Lys Glu Ser Phe Val Leu Lys Lys Lys [SEQ ID NO:4], wherein the length of the polylysine string can vary. The synthetic oligonucleotides employed for fiber amplification were the primer TCCC CCCGGG TCTAGA TTA GGA TCC TTC TTG GGC AAT GTA TGA [SEQ ID NO:11], and the primer CGT GTA TCC ATA TGA CAC AGA [SEQ ID NO:12], as illustrated in FIGS. 4C and 4D, respectively.

The amplified gene product was then cut with the restriction enzymes NdeI and BamHI, and was cloned into the NdeI/BamHI sites of the fiber-minus plasmid pAd NS 83-100 to create the transfer vector pAd NS 83-100 UTV. The entire NdeI to SalI adenovirus sequence of pAd NS 83-100 UTV was cloned into the fiber-minus plasmid pAd BS 59-100 to create pAd BS 59-100 UTV.

The UTV adenovirus vector was created through homologous recombination in 293 cells. Namely, the E4+ pAd BS 59-100 UTV transfer vector was linearized with SalI, and was transfected into 293 cells that were previously infected with the adenovirus vector, A2F. The A2F vector was derived from a GV10 vector. The Ad5-based vector GV10 contains the lacZ gene under the control of the Rous sarcoma virus promoter (i.e., comprises RSV lacZ). The insertion of the reporter gene in GV10 is made within the E1 region (i.e., the vector is E1−). The GV10 vector also contains a deletion of the E3 region, but is E4+. In comparison with GV10 (i.e., RSV lacZ E1− E3− E4+), A2F further comprises a deletion of the essential E4 adenovirus genes, but is E3+ (i.e., RSV lacZ E1− E3+ E4−).

The 293 cells contain an E1 complementing sequence, but do not contain an E4 complementing sequence. The lack of an E4 complementing sequence prevents replication of the E4− A2F vector in the 293 cell line. However, upon co-introduction of A2F virus and pAd BS 59-100 UTV in 293 cells, homologous recombination takes place between the UTV transfer vector and the A2F adenoviral genome, producing an E3+E4+ adenovirus genome comprising a chimeric fiber protein, which is capable of replication in 293 cells. This particular resultant UTV vector was designated GV10 UTV.

The GV10 UTV vector was isolated using standard plaque isolation techniques with 293 cells. Following three successive rounds of plaque-purification, the GV10 UTV vector contained the fiber mutation and was free of any contamination by the E4⁻ A2F vector. The presence of the chimeric fiber sequences in the GV10 UTV vector was confirmed by sequencing the fiber mRNA using reverse transcriptase-polymerase chain reaction (RT-PCR), which validated the presence of a polyadenosine tail in the chimeric fiber mRNA.

Similarly, the production of a chimeric fiber protein by the vector was confirmed by Western blot. To accomplish this, 293 cells were infected at a multiplicity of infection (MOI) of 5 with either GV10 comprising wild-type adenoviral fiber protein or with GV10 UTV comprising chimeric fiber protein. At two days post-infection, the cells were washed and then lysed in PBS by three freeze-thaw cycles. The lysates were cleared by centrifugation and loaded onto a 10% sodium dodecyl sulfate/polyacrylamide gel. Following electrophoresis, the proteins were transferred onto nitrocellulose and detected by chemiluminescence using a polyclonal antibody to fiber. The migration of the proteins indicated that the chimeric UTV fiber is about 1.5 to about 2.0 kilodaltons larger than the unmodified 62 kilodalton WT fiber protein.

These results confirm that the method identified herein can be employed to introduce modifications into the fiber protein to produce a chimeric fiber protein. Similar techniques can be employed to introduce modifications into the hexon or penton proteins, or to introduce similar modifications (e.g., the addition of a string of amino acids comprised of arginine, lysine and/or histidine, or comprised of aspartate and/or glutamate, or the addition of any of these sequences into a coding region of the coat proteins).

EXAMPLE 3

This example describes the binding to cells of an adenoviral vector comprising a chimeric coat protein such as a chimeric fiber protein as compared with a wild-type adenoviral vector, either in the presence or absence of added soluble wild-type fiber protein.

For these experiments, the cells identified in Example 1 to which adenovirus binds with either high efficiency (i.e. receptor-plus cells) or low efficiency (i.e., receptor-minus cells) were employed. The epithelial cell line A549 was used as representative of receptor-plus cells, and the fibroblast cell line HS 68 was used as representative of receptor-minus cells. Confluent monolayers of either A549 or HS 68 cells were preincubated at 4° C. with concentrations of soluble fiber protein ranging from 0 to about 10 μg/ml. The GV10 UTV vector comprising chimeric fiber protein (UTV) or GV10 vector comprising wild-type fiber protein (WT) were labeled with tritiated thymidine as described in Example 1. About 20,000 cpm of [$^3$H]-thymidine labeled GV10 UTV or GV10 vector were then incubated with the cells for about 2 hours at 4° C. The cells were washed three times with cold PBS, and the cell-associated cpm were determined by scintillation counting. Results were obtained as the average of duplicate measurements and are presented in FIGS. 5A and 5B for the A549 and HS 68 cell lines, respectively.

Figure 5A:
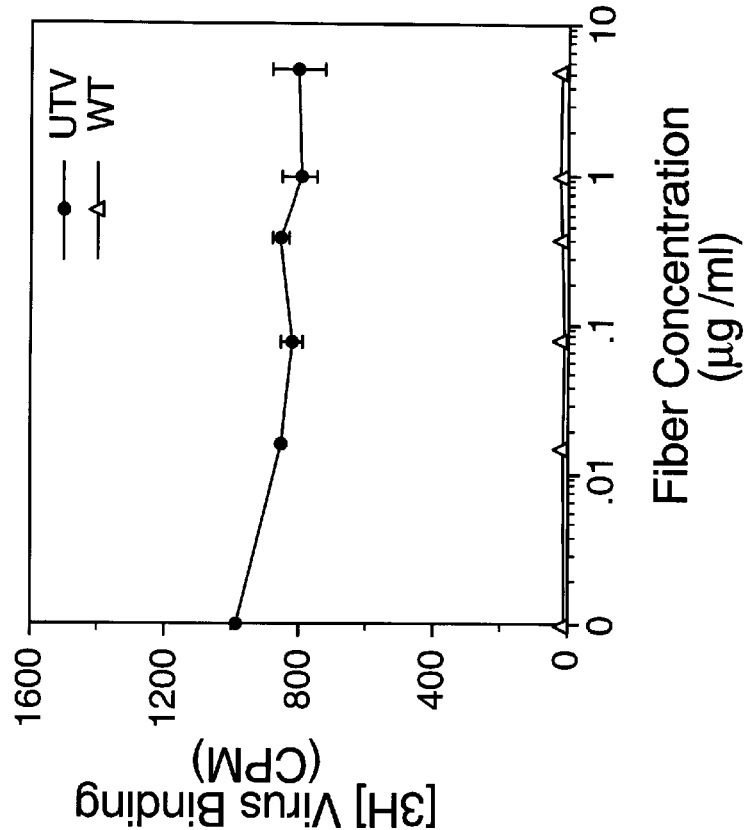
FIGS. 5A–B are graphs depicting a comparison of the binding of an adenoviral vector comprising wild-type fiber protein (i.e., GV10, Δ) and adenoviral vector comprising chimeric fiber protein (i.e., GV10 UTV, ●) to a receptor-plus (A549, FIG. 5A) and a receptor-minus (HS 68, FIG. 5B) cell.
Figure 5B:
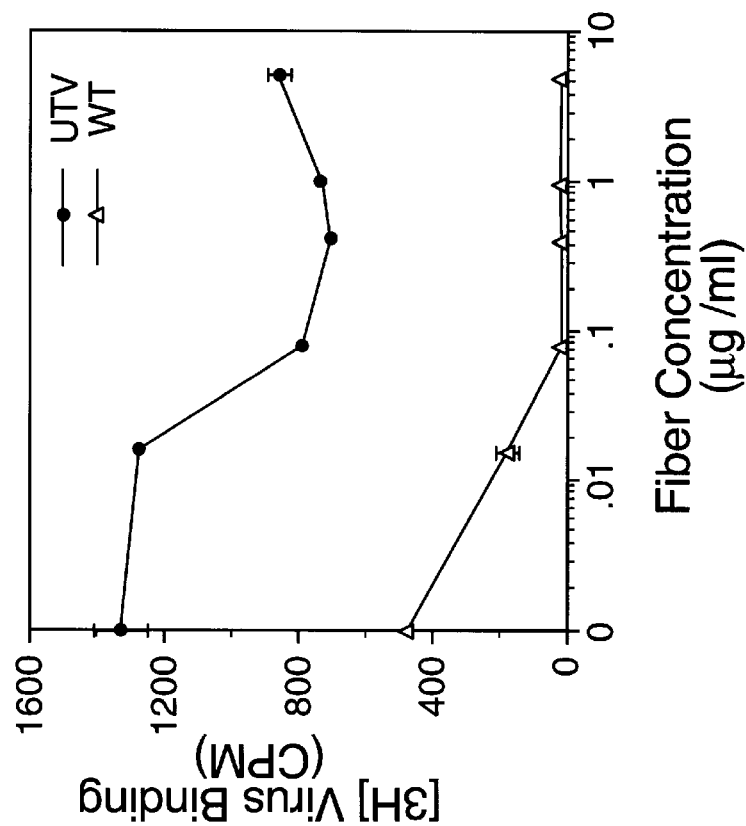

As can be seen in FIGS. 5A–B, the GV10 UTV vector chimeric fiber protein was able to bind both receptor-plus (FIG. 5A) and receptor-minus (FIG. 5B) cells with high efficiency. In comparison, the GV10 vector comprising wild-type fiber was more effective at binding to receptor-plus cells. In particular, radiolabeled GV10 UTV bound to cells expressing detectable levels of fiber receptor (i.e., A549 alveolar epithelial cells) about 2- to 2.5-fold better than GV10. Whereas all of the binding of the GV10 vector was inhibited by competing recombinant fiber protein, only about 40% of the GV10 UTV vector was inhibited by the addition of competing fiber. No detectable binding of GV10 vector comprising wild-type adenoviral fiber to HS 68 human foreskin fibroblast cells lacking fiber receptor was observed. In comparison, the GV10 UTV vector efficiently bound to HS 68 cells, and the addition of competing fiber protein had no effect on binding.

These results confirm that binding of the GV10 UTV vector comprising a chimeric coat protein (i.e., a chimeric fiber protein) does not occur via the wild-type adenoviral fiber receptor, and instead occurs via a heretofore unrecognized fiber receptor. Moreover, the results confirm that incorporation of a chimeric coat protein such as a chimeric fiber protein into an adenoviral vector results in an improved adenoviral vector. Namely, the modification comprised by the GV10 UTV vector enables it overcome the aforementioned relative inability of wild-type adenovirus to bind to receptor-minus cells, in particular, non-epithelial cells, and also allows the modified vector to bind to receptor-plus cells with an increased efficiency.

EXAMPLE 4

This example describes an investigation of the ability of various soluble factors, and inhibitors of these soluble factors, to block binding of adenovirus comprising chimeric fiber protein to receptor-minus HS 68 fibroblast cells.

For these experiments, the inhibition of GV10 UTV binding by various negatively charged molecules including salmon sperm DNA, mucin, chondroitin sulfate, and heparin, was assessed. Chondroitin sulfate and heparin are negatively charged molecules which get their charge from sulfate groups. Mucin is negatively charged due to the presence of sialic acid moieties, and DNA is negatively charged due to its incorporation of phosphate moieties. About 20,000 cpm of UTV in 250 μl of binding buffer (i.e., Dulbecco's Modified Eagle Media (D-MEM) was incubated at room temperature for about 30 minutes with concentrations of negatively charged molecules ranging from about $1 \times 10^{-3}$ to about $1 \times 10^4$ μg/ml. Following incubation, the mixtures were chilled on ice, and were then added to prechilled HS 68 cells plated in 24 well plates. The cells were incubated for about 1 hour, and then the cells were washed three times with PBS. Cell-associated cpm were determined by scintillation counting, and reported as the average of duplicate measurements.

Figure 6:
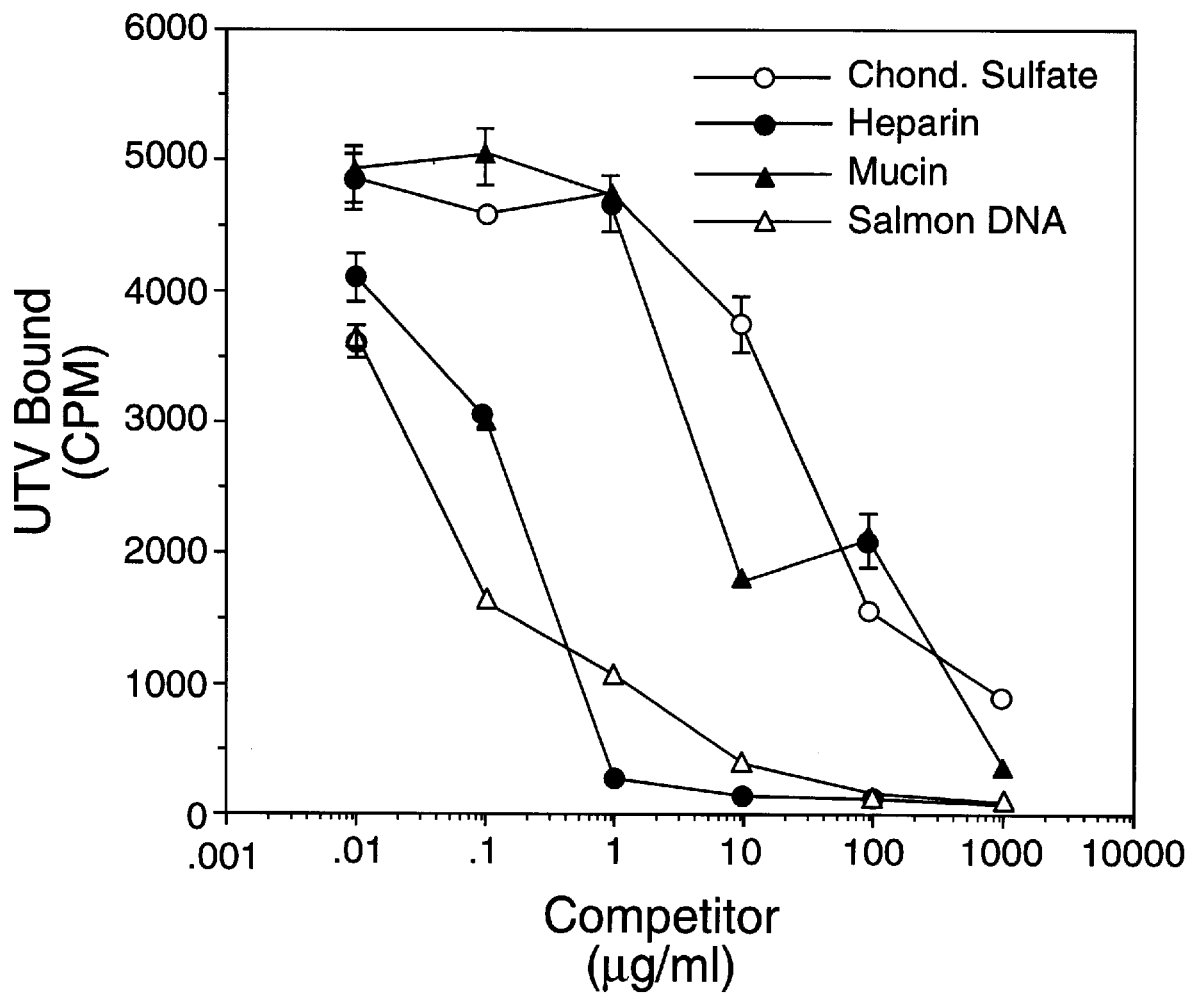
FIG. 6 is a graph of UTV bound (counts per minute (CPM)) versus amount of competitor (μg/ml) for inhibition of binding of chimeric adenoviral fiber protein to receptor-minus cells (i.e., HS 68 fibroblasts) by the soluble factors chondrotin sulfate (○); heparin (●); mucin (▲); and salmon sperm DNA (Δ).

As indicated in FIG. 6, whereas the presence of competing wild-type fiber protein had no effect on binding of a GV10 UTV vector (i.e., comprising chimeric fiber) to HS 68 cells, negatively-charged competing molecules were able to block GV10 UTV binding. All four molecules were able to inhibit GV10 UTV binding to HS 68 cells, although heparin and DNA were most effective. These molecules have no significant effect on the binding of a GV10 vector (i.e., comprising wild-type fiber) to cells expressing high levels of fiber receptor (i.e., A549 cells; data not shown).

These results confirm that negatively charged molecules are able to block binding of the GV10 UTV vector to cells mediated by chimeric fiber protein. This inhibition presumably is due to the binding of the negatively charged molecules to the positively charged polylysine residues present on the GV10 UTV fiber. Accordingly, the impact of enzymes which cleave these negatively charged molecules on binding to cells of the GV10 UTV vector was assessed.

HS 68 cells were plated in 24 well plates, and were preincubated with the dilutions of heparinase (Sigma, St. Louis, Mo.), chondroitinase (Sigma), and sialidase (Boehringer Mannheim, Inc.) ranging from about 0.0001 to 1 for 45 minutes at 37° C., followed by 15 minutes at 4° C. Whereas chondroitinase cleaves chondroitin sulfate, heparinase cleaves heparin and heparin sulfate, and sialidase cleaves sialic acid. The initial starting concentrations for dilutions were as follows: heparinase, 25 U/ml (U=0.1 μmole/hour, pH=7.5, 25° C.); chondroitinase, 2.5 U/ml (U=1.0 μmole/minute, pH=8.0, 37° C.); and sialidase 0.25 U/ml (U=1.0 μmole/minute, pH=5.5, 37° C.). Following incubation, the cells were washed three times with cold PBS, and were then incubated with 20,000 cpm of labeled GV10 UTV vector for about 1 hour at 4° C. The cells were then washed three times with cold PBS, and the cell-associated cpm were determined by scintillation counting. The results were reported as the average of duplicate measurements.

Figure 7:
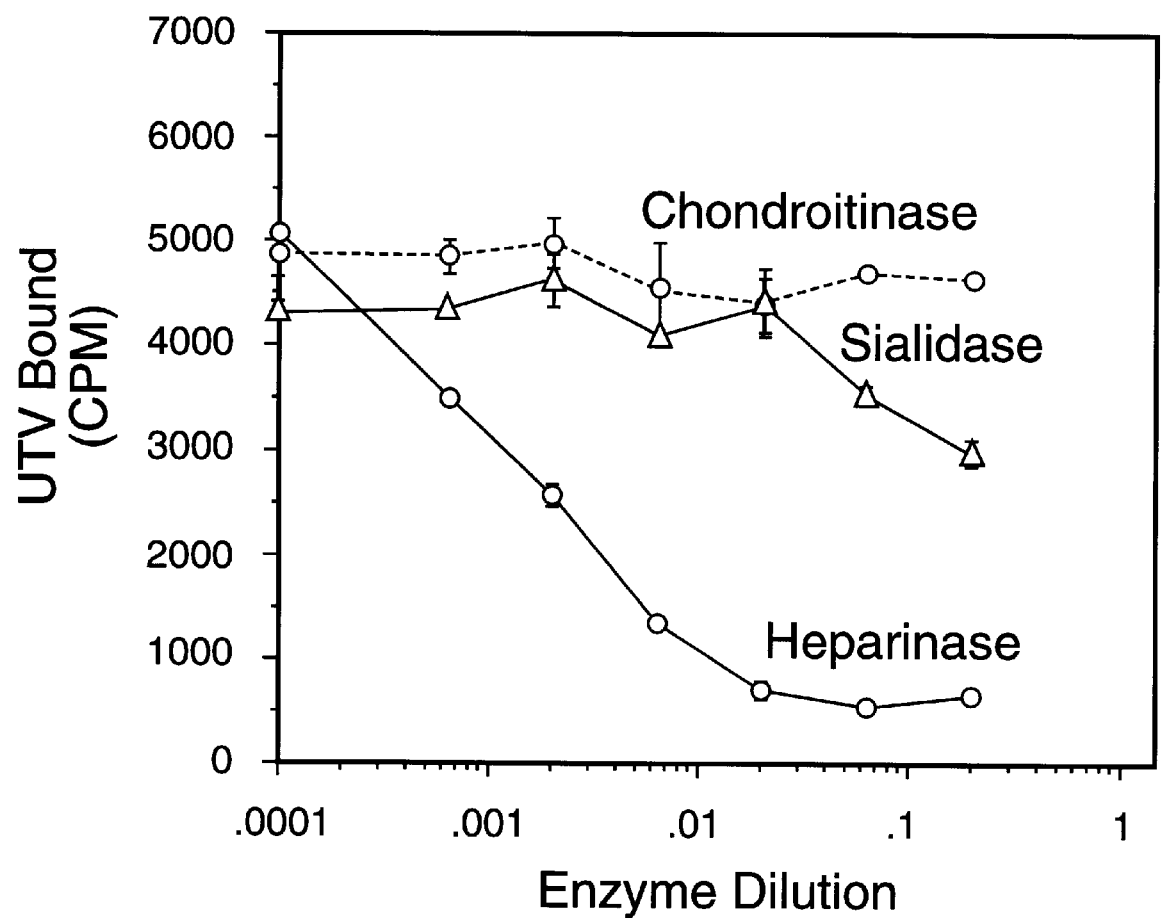
FIG. 7 is a graph of UTV bound (CPM) versus enzyme dilution for inhibition of binding of chimeric adenoviral fiber protein to receptor-minus cells (i.e., HS 68 fibroblasts) by the enzymes chondroitanase (open circles, stippled lines); heparinase (open circles, solid lines); and sialidase (triangles, solid lines).

As illustrated in FIG. 7, pretreatment of HS 68 cells with enzymes that remove negatively charged molecules from the cell surface confirms that the GV10 UTV vector comprising the chimeric fiber protein interacts with negatively charged sites on the cell surface. In particular, heparinase and sialidase were both able to reduce GV10 UTV binding, although heparinase was more effective than sialidase on HS 68 cells.

Thus, these results confirm that a vector comprising chimeric fiber protein (e.g. a GV10 UTV vector), unlike wild-type adenovirus, interacts in a novel fashion with negatively charged molecules on the cell surface to effect cell entry. These results further demonstrate that a vector comprising negatively charged residues (e.g., aspartate and glutamate) instead of positively charged molecules (e.g., lysine) similarly can be employed to bind to and effect cell entry via positively charged molecules present on the cell surface.

EXAMPLE 5

This example evaluate gene delivery to different types of cells mediated by an adenoviral vector comprising chimeric coat protein such as chimeric fiber protein (e.g., GV10 UTV) as compared to gene delivery mediated by adenovirus comprising wild-type coat protein such as fiber protein (e.g., GV10).

For these experiments, the relative levels of lacZ gene delivery by a vector containing the wild-type fiber protein (i.e., GV10) as compared with vector containing chimeric fiber protein (i.e., GV10 UTV) were compared in epithelial-like cells (i.e., HeLa, A549, HepG2 and H700 T cells), smooth muscle cells (i.e., HA SMC and HI SMC cells), endothelial cells (i.e., HUVEC and CPAE cells), fibroblast cells (i.e., HS 68 and MRC-5 cells), glioblastoma cells (i.e., U118 cells) and monocyte macrophages (i.e., THP-1 cells). Approximately $2\times10^5$ cells were inoculated one day prior to transduction by adenovirus into 24 multiwell plates. Each well was then infected at an MOI of 1 with GV10 (i.e., comprising wild-type adenoviral fiber protein) or with GV10 UTV (i.e., comprising chimeric adenoviral fiber) in a 250 μl volume for about one hour. The wells were then washed and incubated for two days, after which the lacZ activity of the cell lysates was determined. The results were reported as the average of duplicate measurements.

Figure 8:
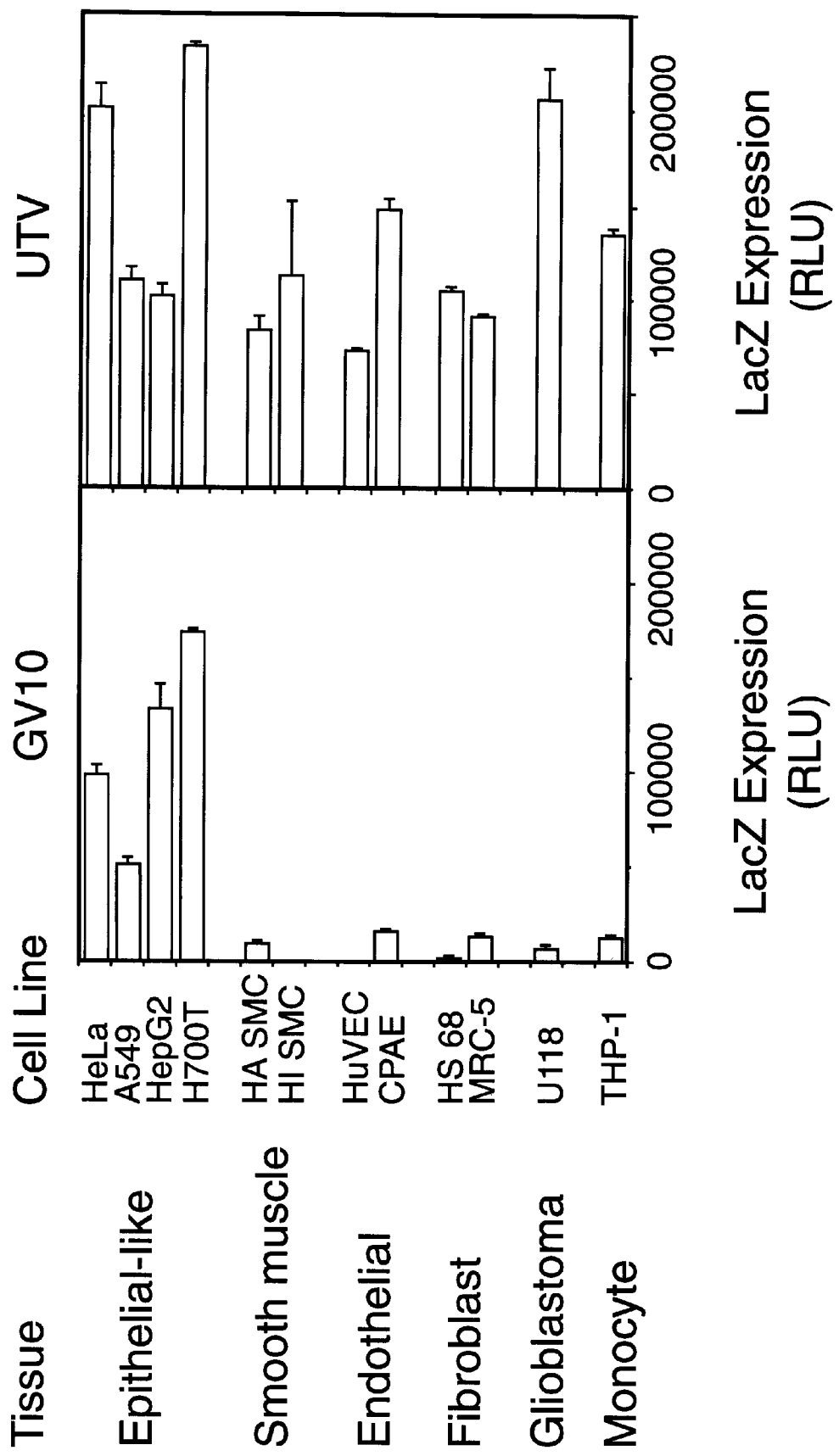
FIG. 8 is a bar graph depicting a comparison of transfer of a lacZ reporter gene by an adenoviral vector comprising wild-type fiber protein (i.e., GV10) and an adenoviral vector comprising chimeric fiber protein (i.e. GV10 UTV) as assessed by resultant reporter gene expression (i.e., relative light units (RLU)) in various receptor-plus and receptor-minus cells.

As illustrated in FIG. 8, the use of the GV10 UTV vector to transfer a reporter gene to a panel of cell lines confirms that the presence of the chimeric fiber protein (UTV) increases lacZ gene delivery to cells expressing low or undetectable levels of fiber receptor (i.e., receptor-minus cells) from about 5- to about 300-fold as compared with wild-type vector (GV10). In cells expressing high levels of the fiber receptor (i.e., receptor-plus cells), the incorporation of the chimeric fiber protein in the GV10 UTV vector results in an increase in gene delivery of up to about 3-fold.

This reduction in expression observed with transduction of receptor-minus non-epithelial cells as compared with receptor-plus epithelial cells by adenovirus comprising a wild-type fiber protein (i.e., GV10) directly correlates with the relative ability of the vector to bind these different cell types, as reported in Example 3. These results support the view that the low expression of receptors for wild-type adenovirus fiber protein is a significant limiting factor to their efficient transduction by current adenovirus vectors.

Similarly, the ability of the chimeric coat protein (i.e., the chimeric fiber protein) to augment gene transfer in vivo was assessed. Three BALB/c mice were inoculated intranasally with about $1\times10^8$ pfu of GV10 in 50 μl of a saline solution comprising 10 mM $MgCl_2$ and 10 mM Tris (pH 7.8). Another three mice received the same dose of GV10 UTV, and two mice received the saline solution alone. The animals were sacrificed at two days post-administration, and the lungs were assayed for lacZ activity. The lungs were prepared for analysis by snap-freezing the lung in liquid nitrogen, grinding the tissue with a mortar and pestle, and lysing the ground tissue in 1.0 ml of lacZ reporter lysis buffer (Promega Corp., Madison, Wis.). A fluorometric assay was used to monitor lacZ activity, and the results of the experiments were reported as the average activity measured from each group of animals.

Figure 9:
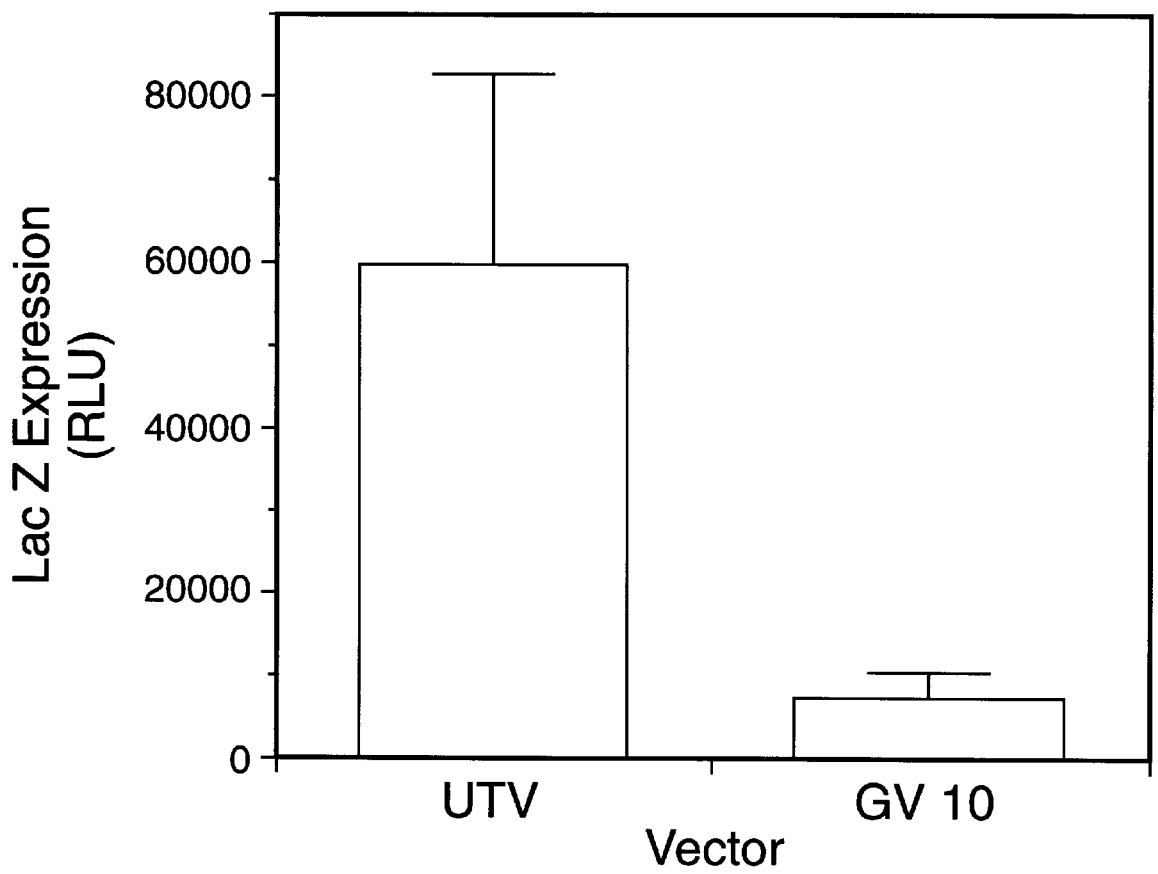
FIG. 9 is a bar graph depicting a comparison of transfer of a lacZ reporter gene by an adenoviral vector comprising wild-type fiber protein (i.e., GV10) and an adenoviral vector comprising chimeric fiber protein (i.e., GV10 UTV) as assessed by resultant reporter expression (i.e., relative light units (RLU)) in mouse lung.

The results of these experiments are illustrated in FIG. 9. As can be seen from this Figure, gene transfer in vivo mediated by the GV10 UTV vector comprising chimeric fiber protein (UTV) as compared with a vector comprising wild-type fiber protein (GV10) resulted in an average of 8-fold higher delivery to mouse lung.

These results thus confirm that incorporation of a chimeric coat protein (in this case, a chimeric fiber protein) in an adenoviral vector substantially increases the efficiency of vector-mediated gene delivery both in vitro and in vivo as compared to an adenovirus vector comprising wild-type fiber protein. Moreover, the results support the conclusion that low fiber receptor expression is a significant factor contributing to the suboptimal delivery observed in the lung and in other tissues. Also, the results confirm the superiority of the GV10 UTV vector, as well as other similar UTV vectors, over other currently available adenoviral vectors for gene transfer (e.g., delivery of the CFTR gene) to the lung and other tissues.

EXAMPLE 6

This example evaluates the ability of a vector according to the invention comprising a chimeric coat protein (e.g., a chimeric fiber protein) to interact with passenger DNA by means of a protein/DNA interaction, and to thereby carry the DNA into the cell in a "piggy-back" fashion.

For these experiments, an adenoviral vector comprising wild-type fiber (i.e., GV10) and an adenoviral vector comprising chimeric fiber (i.e., GV10 UTV) were used to assess gene transfer to receptor-plus epithelial cells (i.e., 293, A549, and H700 T cells). In control experiments, the cells were transduced with the vectors as previously described. In the experimental condition, the vectors were incubated with the plasmid pGUS, which comprises a β-glucuronidase reporter gene, such that the chimeric adenoviral fiber protein was able to complex with the plasmid DNA. Specifically, about 5×10⁷ active particles (i.e., fluorescence focus units (ffu)) of GV10 or GV10 UTV were incubated for 1 hour with about 2.5 μg of plasmid pGUS DNA. The mixture was then added to about 2×10⁵ of the indicated cells in 250 μl of DMEM containing 10% fetal bovine serum. Both β-glucuronidase and β-galactosidase activity were then assessed by fluorometric assay at 10 days post-transduction. β-glucuronidase expression in cells was monitored similarly to the β-galactosidase assay for lacZ expression, by monitoring the generation of a blue color when β-glucuronidase catalyzes a reaction with the substrate X-glu.

Figure 10:
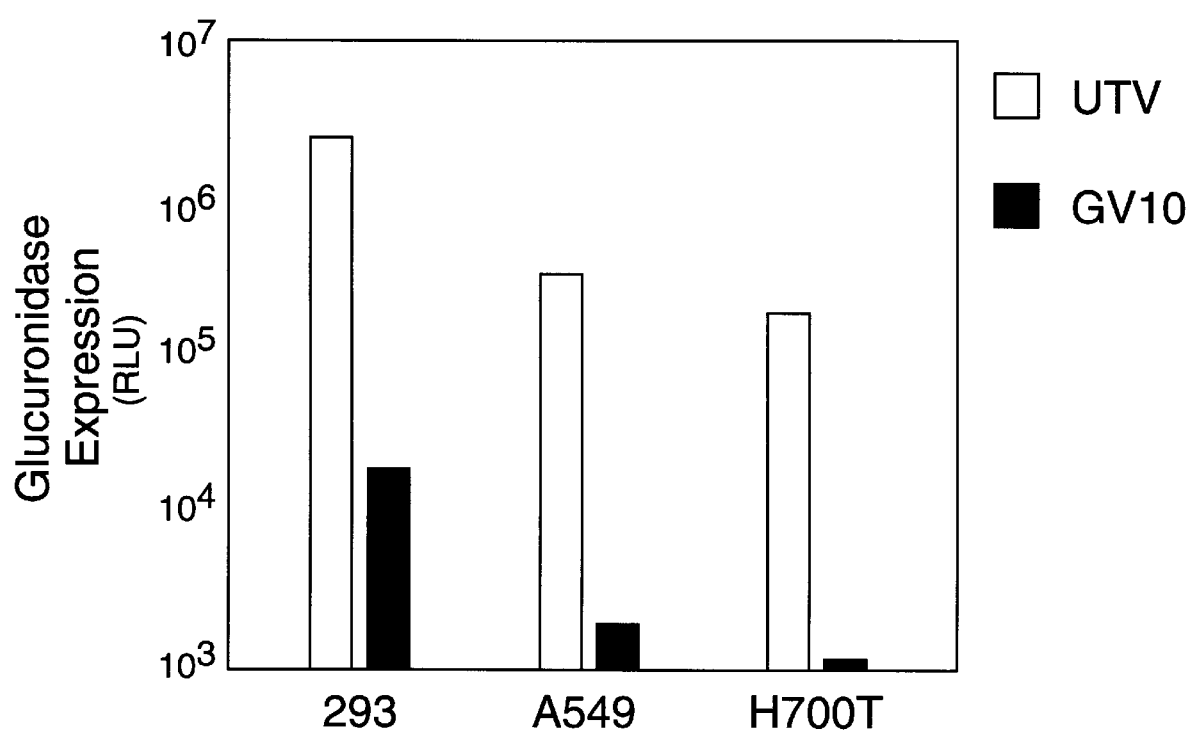
FIG. 10 is a bar graph depicting the transfer of a reporter gene (i.e., contained in pGUS) by an adenoviral vector comprising wild-type fiber protein (i.e., GV10, solid bars) and an adenoviral vector comprising chimeric fiber (i.e., GV10 UTV, open bars) potentially bound via a protein/DNA interaction into 293 cells, A549 cells, and H700 T cells.

The results of these experiments are illustrated in FIG. 10. Comparable levels of lacZ expression were obtained when either a GV10 vector (i.e. comprising wild-type fiber protein) or a GV10 UTV vector (i.e. comprising chimeric fiber protein) were employed to transfer the reporter gene in cis to epithelial cells. In comparison, the wild-type vector was able to transfer intracellularly the plasmid pGUS at only a relatively low level in all epithelial cells, as assessed by β-glucuronidase gene expression. This basal level of gene transfer likely was accomplished by means of receptor-mediated uptake (RME) of bystander molecules, as previously described (PCT patent application WO 95/21259). However, with use of a GV10 UTV vector comprising a chimeric fiber protein, transfer of the pGUS plasmid was substantially increased. In the case of gene transfer to 293 cells, pGUS plasmid-directed β-glucuronidase expression exceeded expression observed following GV10 UTV-vector mediated transfer of a cis-linked reporter gene.

These results confirm that a vector comprising a chimeric coat protein such as a chimeric fiber protein according to the invention demonstrates increased transfer of a nucleic acid that is not located in cis with the vector. Ostensibly, this enhanced gene transfer is effected by the occurrence of a protein/DNA interaction between the positively charged residues on the chimeric fiber (e.g., residues of the polylysine string), resulting in binding to the vector of the nucleic acid; however, other means of enhancement also are possible.

All of the references cited herein, including patents, patent applications, and publications, are hereby incorporated in their entireties by reference to the same extent as if each reference were set forth in its entirety herein.

While this invention has been described with an emphasis upon preferred embodiments, it will be apparent to those of ordinary skill in the art that variations in the preferred embodiments can be prepared and used and that the invention can be practiced otherwise than as specifically described herein. The present invention is intended to include such variations and alternative practices. Accordingly, this invention includes all modifications encompassed within the spirit and scope of the invention as defined by the following claims.

What is claimed is:

1. A chimeric adenovirus coat protein comprising a nonnative amino acid sequence, wherein said chimeric adenovirus coat protein directs entry into cells of a vector comprising said chimeric adenovirus coat protein that is more efficient than entry into cells of a vector that is identical except for comprising a wild-type adenovirus coat protein rather than said chimeric adenovirus protein, and wherein said chimeric adenovirus coat protein binds a novel endogenous binding site present on the cell surface.

2. The chimeric adenovirus coat protein of claim 1, wherein said nonnative amino acid sequence is inserted into or in place of an internal coat protein sequence.

3. The chimeric adenovirus coat protein of claim 1, wherein said nonnative amino acid sequence is at or near the C-terminus of said protein.

4. The chimeric adenovirus coat protein of claim 1, wherein said nonnative amino acid sequence is linked to said protein by a spacer sequence of from about 3 to about 30 amino acids.

5. The chimeric adenovirus coat protein of claim 1, wherein said nonnative amino acid sequence comprises from about 3 to about 30 amino acids.

6. The chimeric adenovirus coat protein of claim 5, wherein said nonnative amino acid sequence comprises amino acids selected from the group consisting of lysine, arginine, and histidine.

7. The chimeric adenovirus coat protein of claim 5, wherein said nonnative amino acid sequence comprises amino acids selected from the group consisting of aspartate and glutamate.

8. The chimeric adenovirus coat protein of claim 5, wherein said nonnative amino acid sequence comprises a sequence selected from the group consisting of SEQ ID NO:1, SEQ ID NO:2, and SEQ ID NO:3, and wherein said sequence may be deleted at the C-terminus by 1, 2, 3, 4, or 5 residues.

9. The chimeric adenovirus coat protein of claim 8, wherein said chimeric adenovirus coat protein is a chimeric adenovirus hexon protein or a chimeric adenovirus penton protein.

10. A chimeric adenovirus fiber protein comprising a nonnative amino acid sequence, wherein said chimeric adenovirus fiber protein directs entry into cells of a vector comprising said chimeric adenovirus fiber protein that is more efficient than entry into cells of a vector that is identical except for comprising a wild-type adenovirus fiber protein rather than said chimeric adenovirus fiber protein, and wherein said fiber protein comprises a sequence selected from the group consisting of SEQ ID NO:4 and SEQ ID NO:5, and wherein the length of the polylysine string can vary from about 3 to about 30 residues.

11. The chimeric adenovirus coat protein of claim 1, wherein said chimeric adenovirus coat protein forms homotrimers in aqueous solutions.

12. The chimeric adenovirus coat protein of claim 1, wherein said chimeric adenovirus coat protein can fold to allow the coat protein to be incorporated into an adenovirus.

13. The chimeric adenovirus coat protein of claim 1, wherein said chimeric adenovirus coat protein is a fiber protein.

14. The chimeric adenovirus coat protein of claim 13, wherein said fiber protein comprises a sequence selected from the group consisting of SEQ ID NO:1, SEQ ID NO:2, and SEQ ID NO:3, and wherein said sequence may be deleted at the C-terminus by 1, 2, 3, 4, or 5 residues.

15. The chimeric adenovirus coat protein of claim 1, wherein said chimeric adenovirus coat protein is a penton protein or a hexon protein.

16. An isolated and purified nucleic acid encoding a chimeric adenovirus coat protein of claim 1, wherein the nucleic acid sequence that encodes said nonnative amino acid sequence comprises SEQ ID NO:6 located prior to the polyadenylation site.

17. The nucleic acid of claim 16, wherein said chimeric adenovirus coat protein is a fiber protein.

18. The nucleic acid of claim 16, wherein said chimeric adenovirus coat protein is a penton protein or a hexon protein.

19. An isolated and purified nucleic acid comprising a sequence selected from the group consisting of SEQ ID NO:7, and SEQ ID NO:8, and conservatively modified variants thereof.

20. The vector that comprises or encodes the chimeric adenovirus coat protein of claim 1.

21. The vector of claim 20, wherein said vector is a viral vector selected from the group consisting of nonenveloped viruses.

22. The vector of claim 20, wherein said vector is an adenoviral vector.

23. The vector of claim 22, wherein said vector further comprises a nucleic acid comprising a passenger gene.

24. The vector of claim 23, wherein said nucleic acid is inserted into the adenoviral genome.

25. The vector of claim 22, wherein said chimeric adenovirus coat protein is a fiber protein.

26. The vector of claim 25, wherein said fiber protein comprises a sequence selected from the group consisting of SEQ ID NO:1, SEQ ID NO:2, and SEQ ID NO:3, and wherein said sequence may be deleted at the C-terminus by 1, 2, 3, 4, or 5 residues.

27. The vector of claim 22, wherein said chimeric adenovirus coat protein is a penton protein, and said vector does not comprise wild-type fiber protein.

28. The adenoviral vector GV10 UTV.

29. An isolated cell comprising the vector of claim 20.

30. The vector of claim 20, wherein said vector can be propagated in vitro in 293 cells.

31. A vector that comprises or encodes a chimeric adenovirus coat protein comprising a nonnative amino acid sequence, wherein said chimeric adenovirus coat protein binds a novel endogenous binding site present on a cell surface and directs entry into cells of a nucleic acid attached to said chimeric adenovirus coat protein by a protein/DNA interaction more efficiently than a corresponding wild-type adenovirus coat protein.

32. A transfer vector that encodes the chimeric adenovirus coat protein of claim 1.

33. The transfer vector of claim 32, wherein said transfer vector is selected from the group consisting of nonenveloped viruses.

34. The transfer vector of claim 32, wherein said transfer vector is an adenoviral vector.

35. The transfer vector of claim 32, wherein said transfer vector further comprises a nucleic acid encoding a passenger gene.

36. The transfer vector of claim 32, wherein said coat protein is a fiber protein.

37. The transfer vector of claim 36, wherein said fiber protein comprises a sequence selected from the group consisting of SEQ ID NO:6, SEQ ID NO:7, and SEQ ID NO:8, and conservatively modified variants thereof.

38. The transfer vector of claim 32, wherein said chimeric coat protein is a chimeric adenovirus hexon protein or a chimeric adenovirus penton protein.

39. A transfer vector selected from the group consisting of pAd NS 83-100 UTV and pAd BS 59-100 UTV.

40. An adenoviral vector that comprises or encodes a chimeric adenovirus fiber protein comprising a nonnative amino acid sequence, wherein said chimeric adenovirus fiber protein directs entry into cells of a vector comprising said chimeric adenovirus fiber protein that is more efficient than entry into cells of a vector that is identical except for comprising a wild-type adenovirus fiber protein rather than said chimeric adenovirus fiber protein, and wherein said fiber protein comprises a sequence selected from the group consisting of SEQ ID NO:4 and SEQ ID NO:5, and wherein the length of the polylysine string can vary from about 3 to about 30 residues.

41. A method of increasing the efficiency of entry into a cell of a viral vector comprising a coat protein, which method comprises:
   (i) replacing a coat protein of said viral vector with the chimeric adenovirus coat protein of claim 1, and
   (ii) contacting a cell with said viral vector in vitro, such that said vector enters said cell more efficiently than an otherwise identical vector comprising a wild-type adenovirus coat protein.

42. The method of claim 41, wherein said vector is an adenoviral vector that further comprises a nucleic acid comprising a passenger gene.

43. The method of claim 42, wherein said nucleic acid is inserted into the adenoviral genome.

44. A method of increasing the efficiency of introduction of a nucleic acid into a cell, which method comprises;
   (a) obtaining a vector comprising the chimeric adenovirus coat protein of claim 5,
   (b) contacting said viral vector with a nucleic acid comprising a passenger gene such that said chimeric adenovirus coat protein and said nucleic acid bind by a protein/DNA interaction, and
   (c) contacting a cell with said viral vector to which is bound said nucleic acid in vitro, such that said nucleic acid enters said cell more efficiently than an identical nucleic acid contacted with an otherwise identical viral vector comprising a wild-type adenovirus coat protein.

45. A method of making the chimeric adenovirus coat protein of claim 1, comprising introducing a spacer sequence into the coding sequence of said chimeric adenovirus coat protein prior to any stop codon or polyadenylation signal.

46. The method of claim 45, wherein said spacer sequence comprises the sequence of SEQ ID NO:6 or a conservatively modified variant thereof.

47. A method of making an adenoviral vector that comprises or encodes a chimeric adenovirus fiber protein comprising a nonnative amino acid sequence, wherein said chimeric adenovirus fiber protein directs entry into cells of a vector comprising said chimeric adenovirus fiber protein that is more efficient than entry into cells of a vector that is identical except for comprising a wild-type adenovirus fiber protein rather than said chimeric adenovirus fiber protein,
   wherein said method comprises providing to a cell that does not comprise any E4 complementing sequences:
      (a) a linear vector comprising the chimeric fiber and a wild-type E4 gene, and (b) a linear vector that is E4⁻.

48. A method of increasing the efficiency of entry into a cell of a vector comprising a coat protein, which method comprises:
   (i) obtaining a viral vector comprising the chimeric adenovirus coat protein of claim 1 and a nucleic acid comprising a passenger gene, and
   (ii) contacting a cell with said vector in vitro, such that said vector enters said cell more efficiently than an otherwise identical vector comprising a wild-type adenovirus coat protein.

49. The method of claim 48, wherein said nucleic acid is inserted into the viral genome.

50. A method of increasing the efficiency of introduction of a nucleic acid into a cell, which method comprises:
   (i) obtaining a viral vector comprising the chimeric adenovirus coat protein of claim 1 and a nucleic acid comprising a passenger gene, wherein said nucleic acid is bound to said chimeric adenovirus coat protein by means of a protein/DNA interaction, and (ii) contacting a cell with said vector in vitro, such that said nucleic acid enters said cell more efficiently than an identical nucleic acid contacted with an otherwise identical vector comprising a wild-type adenovirus coat protein.

51. In a method of gene therapy comprising the administration to a patient in need of gene therapy a therapeutically effective amount of a viral vector comprising a therapeutic gene that is expressed in said patient, the improvement comprising administering to the patient said viral vector in which a coat protein has been replaced with the chimeric adenovirus coat protein of claim 1.

52. The method of claim 51, wherein said viral vector is an adenoviral vector.

53. The method of claim 51, wherein said therapeutic gene is inserted into the viral vector genome.

54. The method of claim 51, wherein said therapeutic gene is bound to the chimeric adenovirus coat protein by a protein/DNA interaction.

55. In a method of ex vivo gene therapy comprising the administration to a patient in need of ex vivo gene therapy a therapeutically effective amount of transduced cells comprising a viral vector comprising a therapeutic gene that is expressed in said cells, the improvement comprising administering to the patient said transduced cells comprising the viral vector in which a coat protein has been replaced with the chimeric coat protein of claim 1, whereupon said administration, said therapeutic gene is expressed in said patient.

56. The method of claim 55, wherein said viral vector is an adenoviral vector.

57. The method of claim 55, wherein said therapeutic gene is inserted into the viral vector genome.

58. The method of claim 55, wherein said therapeutic gene is bound to the chimeric adenovirus coat protein by a protein/DNA interaction.

59. In a method of gene therapy comprising the administration to a patient in need of gene therapy a therapeutically effective amount of a viral vector comprising a therapeutic gene that is expressed in said patient, the improvement comprising administering to the patient said viral vector in which a coat protein has been replaced with the chimeric adenovirus coat protein of claim 6.

60. The method of claim 59, wherein said viral vector is an adenoviral vector.

61. In a method of ex vivo gene therapy comprising the administration to a patient in need of ex vivo gene therapy a therapeutically effective amount of transduced cells comprising a viral vector comprising a therapeutic gene that is expressed in said cells, the improvement comprising administering to the patient said transduced cells comprising the viral vector in which a coat protein has been replaced with the chimeric coat protein of claim 6, whereupon said administration, said therapeutic gene is expressed in said patient.

62. The method of claim 61, wherein said viral vector is an adenoviral vector.

* * * * *